US008710442B2

United States Patent
Kanda et al.

(10) Patent No.: US 8,710,442 B2
(45) Date of Patent: Apr. 29, 2014

(54) SENSING DEVICE AND ELECTRONIC APPARATUS

(71) Applicant: Seiko Epson Corporation, Tokyo (JP)

(72) Inventors: Eiji Kanda, Yokohama (JP); Hideto Ishiguro, Shiojiri (JP); Tsukasa Eguchi, Matsumoto (JP); Tetsuji Fujita, Chino (JP); Hidetoshi Yamamoto, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/013,874

(22) Filed: Aug. 29, 2013

(65) Prior Publication Data

US 2014/0070100 A1      Mar. 13, 2014

Related U.S. Application Data

(62) Division of application No. 13/439,347, filed on Apr. 4, 2012, now Pat. No. 8,552,378.

(30) Foreign Application Priority Data

Apr. 6, 2011    (JP) .................................. 2011-084243

(51) Int. Cl.
    *G01J 5/00*  (2006.01)
    *A61B 5/117* (2006.01)
(52) U.S. Cl.
    CPC ....................................... *A61B 5/117* (2013.01)
    USPC ..................................................... 250/338.1
(58) Field of Classification Search
    CPC ........ A61B 5/117; G06K 9/008; G06F 21/32;
                                        G06T 7/0012; H04L 9/3231
    USPC .......................................... 250/338.1–338.5
    See application file for complete search history.

(56) References Cited

U.S. PATENT DOCUMENTS

| 6,327,376 | B1 * | 12/2001 | Harkin ........................... 382/124 |
| 6,784,413 | B2 * | 8/2004  | Sasaki et al. ............... 250/214 R |
| 7,369,690 | B2 * | 5/2008  | Joo et al. ........................ 382/124 |
| 8,101,912 | B2 * | 1/2012  | Yamaguchi et al. .......... 250/332 |
| 8,502,681 | B2 * | 8/2013  | Bolling et al. .............. 340/573.1 |
| 2003/0020028 | A1 * | 1/2003 | Iihama et al. .................. 250/556 |
| 2004/0252867 | A1 * | 12/2004 | Lan et al. ..................... 382/124 |
| 2008/0112600 | A1  | 5/2008  | Miura et al. |
| 2008/0205711 | A1 * | 8/2008 | Kishigami et al. ............ 382/115 |
| 2008/0284925 | A1 * | 11/2008 | Han ................................ 349/12 |

(Continued)

FOREIGN PATENT DOCUMENTS

| JP | A-2009-31903  | 2/2009 |
| JP | A-2009-165731 | 7/2009 |

(Continued)

*Primary Examiner* — Kiho Kim
(74) *Attorney, Agent, or Firm* — Oliff PLC

(57) ABSTRACT

A sensing device includes a first electrode, a second electrode with a first opening portion, a light blocking layer with a second opening portion, an organic EL layer including a light emitting unit and being formed between the first electrode and the second electrode, and a light receiving unit. The light blocking layer is positioned in the first electrode or between the first electrode and the second electrode, and in plan view from the subject side, the light blocking layer overlaps the first opening portion and the second opening portion is positioned within the first opening portion, and the light receiving unit is positioned further from the subject side than the second electrode, and in plan view from the subject side, the light receiving unit is positioned within the second opening portion.

5 Claims, 18 Drawing Sheets

(56) References Cited

U.S. PATENT DOCUMENTS

2009/0028396 A1 1/2009 Kishima
2012/0170072 A1* 7/2012 Miyazaki et al. ............ 358/1.13
2012/0241825 A1 9/2012 Aichi

FOREIGN PATENT DOCUMENTS

| JP | A-2009-172263 | 8/2009 |
| JP | A-2009-211730 | 9/2009 |
| JP | A-2010-66944 | 3/2010 |

* cited by examiner

SENSING DEVICE AND ELECTRONIC APPARATUS

This application is a divisional of application Ser. No. 13/439,347 filed Apr. 4, 2012, incorporated herein by reference in its entirety.

BACKGROUND

1. Technical Field

The present invention relates to a sensing device that irradiates light on a subject and that receives the reflected light thereof, and an electronic apparatus.

2. Related Art

There are biometric authentication devices and image scanners in which the image of a subject is read by arranging the light emitting unit and the light receiving unit on the same side with respect to a subject (for example, a finger, a manuscript, or the like) that is placed on a reading region, irradiating light on the subject from the light emitting unit, and receiving the reflected light thereof with the light receiving unit. For example, a biometric information acquisition device 50 that obtains the vein image of a finger 100 by irradiating exit light (near-infrared light) from a light source 6 on the finger 100 by a plurality of reflection faces 11 that are formed on the back face of a light-guide plate 3 and receiving the reflected light from the finger 100 on a light receiving element 1 that includes a plurality of pixels PX is described in JP-A-2009-172263.

However, in the biometric information acquisition device 50 described in JP-A-2009-172263 is the light-guide plate 3 that guides the exit light from a light source 6 with a greater light amount than the reflected light on a light path of the reflected light that is incident on each pixel PX (on a straight line that extends in the vertical direction from each pixel PX). Further, a portion of the exit light from the light source 6 leaks out to the light receiving element 1 side by passing through a low refractive index layer 21 or a reflective layer (semi-reflective layer) 40 that are formed on the back face side of the light-guide plate 3. It is therefore not possible to receive the reflected light from the finger 100 on the light receiving element 1 with high precision. Further, there was a problem that the thickness of the biometric information acquisition device 50 increased due to the light-guide plate 3 or a light blocking layer 2.

SUMMARY

An advantage of some aspects of the invention is that a sensing device that is able to receive reflected light from a subject with high precision while making the device thin and an electronic apparatus using the same.

According to a first aspect of the invention, there is provided a sensing device that includes a light emitting unit, a light receiving unit, and a light blocking layer in which light from the light emitting unit is irradiated on a subject and reflected light from the subject is received by the light receiving unit, wherein the light emitting unit and the receiving unit are provided on the same side with respect to the subject, the light emitting unit is positioned further to the subject side than the light receiving unit, the light emitting unit includes a light emitting layer that emits irradiation light that irradiates the subject, a first electrode that is positioned further to the subject side than the light emitting layer and that transmits the irradiation light and the reflected light, a second electrode that is positioned further to the light receiving unit side than the light emitting layer, blocks the irradiation light and the reflected light, and on which a first opening portion is formed, and an insulating layer that is positioned to correspond to the first opening portion, transmits the irradiation light and the reflected light, and partially insulates the first electrode and the second electrode, wherein the light receiving unit includes a light receiving element that receives the reflected light, the light blocking layer is provided at a position that corresponds to the first opening portion, blocks the irradiation light and the reflected light, and has a second opening portion formed thereon, and in a case when viewed in a plan view from the subject side, the light blocking layer overlaps the first opening portion and a light receiving face of the light receiving element is positioned within the second opening portion.

According to such a configuration, in a case when viewed in a plan view from the subject side, the positions that correspond to the light receiving faces of the light receiving elements and the vicinity thereof out of the light emitting layer (portion corresponding to the first opening portion) is a non-light emitting region that is insulated by the insulating layer and that therefore does not emit irradiation light. There is therefore no light emitting region that emits irradiation light with a greater light amount than reflected light on a light path of reflected light that is incident on the light receiving face of a light receiving element. Further, since portions other than the second opening portion are blocked by the light blocking layer and the second electrode, from out of the reflected light, reflected light from directly above is incident on the light receiving face of a light receiving element from the subject. Further, the irradiation light that exits from the light emitting layer (light emitting region) can also be suppressed from passing through the first opening portion and being directly incident on the light receiving face of a light receiving element by the light blocking layer and the second electrode. It is accordingly possible to receive reflected light from the subject by the light receiving element with high precision. Further, although it is necessary to provide the first electrode, the second electrode, the light emitting layer, the insulating layer, and the light blocking layer, since each such element is formed to be extremely thin, compared to the invention described in JP-A-2009-172263, it is possible to make the thickness of the sensing device thin.

Here, the subject may be a portion of a living body (for example, a finger, the palm of a hand, the back of a hand, the eyes, or the like) or may be a document, paper on which an image is printed, an OHP (OverHead Projector) sheet, or the like. Further, the wavelength of the light that the light emitting layer emits is able to be arbitrarily determined. That is, irradiation light and reflected light may be, for example, near-infrared light or visible light. Further, with the first electrode and the second electrode, the first electrode may be the anode and the second electrode may be the cathode, or the first electrode may be the cathode and the second electrode may be the anode. Further, the shape of the opening portion of the second electrode or the shape of the light receiving face of a light receiving element is able to be arbitrarily determined as a rectangle, a circle, an ellipse, a hexagon, or the like. Further, the size of the opening portion and the size of the light receiving face may be smaller for the second opening portion than for the light receiving face, or vice versa, or both may have the same size. Further, it is not strictly necessary that all of the light receiving faces be positioned within the second opening portion, and it is sufficient if at least a portion of the light receiving faces are positioned within the second opening portion. Further, the light blocking layer can be provided, for example, at positions indicated by BM in FIGS. 2, 17, and 18.

According to a second aspect of the invention, there is provided a sensing device that includes a light emitting unit, a light receiving unit, and a light blocking layer in which light from the light emitting unit is irradiated on a subject and reflected light from the subject is received by the light receiving unit, wherein the light emitting unit and the light receiving unit are provided on the same side with respect to the subject, and the light emitting unit is positioned further to the subject side than the light receiving unit, wherein the light emitting unit includes a light emitting layer that emits irradiation light that irradiates the subject, a first electrode that is positioned further to the subject side than the light emitting layer and that transmits the irradiation light and the reflected light, a second electrode and a third electrode that are positioned further to the light receiving unit side than the light emitting layer, block the irradiation light and the reflected light, and that are provided separately from each other, and an insulating layer that is provided at a position that corresponds to a separating region between the second electrode and the third electrode, transmit the irradiation light and the reflected light, and partially insulates the second and third electrodes and the first electrode, wherein the light receiving unit includes a light receiving element that receives the reflected light, the light blocking layer is provided at a position that corresponds to the separating region, blocks the irradiation light and the reflected light, and has an opening portion formed thereon, and in a case when viewed in a plan view from the subject side, the light blocking layer overlaps the separating region and a light receiving face of the light receiving element is positioned within the opening portion.

Such a configuration also has an effect that is similar to the sensing device according to the first aspect. That is, instead of one second electrode that includes an opening portion, two electrodes (a second electrode and a third electrode) that are provided apart from each other may be used. Here, even in the case of such a configuration, the first electrode may be the anode and the second and third electrodes may be the cathodes, or the first electrode may be the cathode and the second and third electrodes may be the anodes.

Further, with the sensing device according to the first aspect, the light blocking layer may be provided between the subject side of the first electrode to the second electrode. Similarly, with the sensing device according to the second aspect, the light blocking layer may also be provided between the subject side of the first electrode to the second and third electrodes.

Further, according to a third aspect of the invention, there is provided a sensing device that includes a light emitting unit, a light receiving unit, and a plurality of light blocking layers in which light from the light emitting unit is irradiated on a subject and reflected light from the subject is received by the light receiving unit, wherein the light emitting unit and the light receiving unit are provided on the same side with respect to the subject, and the light emitting unit is positioned further to the subject side than the light receiving unit, wherein the light emitting unit includes a light emitting layer that emits irradiation light that irradiates the subject, a first electrode that is positioned further to the subject side than the light emitting layer and that transmits the irradiation light and the reflected light, a plurality of second electrodes that are positioned further to the light receiving unit side than the light emitting layer, block the irradiation light and the reflected light, and that are provided separately from one another, and a plurality of insulating layers that are provided at positions that correspond to separating regions for every separating region between adjacent second electrodes, transmit the irradiation light and the reflected light, and partially insulate the first electrode and the second electrodes, wherein the light receiving unit includes a plurality of light receiving elements that receive the reflected light, each of the plurality of light blocking layers are provided at positions that correspond to the separating regions that are different from one another, block the irradiation light and the reflected light, and on which one or more opening portions are formed, and in a case when viewed in a plan view from the subject side, each of the separating regions overlap the light blocking layers, and one light receiving face of the light receiving element is positioned within each of the opening portions.

Such a configuration also has an effect that is similar to the sensing device according to the first aspect. That is, the configuration may include a plurality of each of the second electrode, the insulating layer, and the light blocking layer in addition to including a plurality of light receiving elements.

Further, according to a fourth aspect of the invention, there is provided a sensing device that includes a light emitting unit, a light receiving unit, and a plurality of light blocking layers in which light from the light emitting unit is irradiated on a subject and reflected light from the subject is received by the light receiving unit, wherein the light emitting unit and the light receiving unit are provided, on the same side with respect to the subject, and the light receiving unit is positioned further to the subject side than the light receiving unit, wherein the light emitting unit includes a light emitting layer that emits irradiation light that irradiates the subject, a plurality of first electrodes that are positioned further to the subject side than the light emitting layer, transmit the irradiation light and the reflected light, and that are provided separately from one another, a plurality of second electrodes that are positioned further to the light receiving unit side than the light emitting layer, block the irradiation light and the reflected light, that are provided separately from one another, and that intersect the plurality of first electrodes, and a plurality of insulating layers that are provided at positions that correspond to separating regions for every separating region between adjacent second electrodes, transmit the irradiation light and the reflected light, and partially insulate the first electrodes and the second electrodes, wherein the light receiving unit includes a plurality of light receiving elements that receive the reflected light, each of the plurality of light blocking layers are provided at positions that correspond to the separating regions that are different from one another, block the irradiation light and the reflected light, and on which one or more opening portions are formed, and in a case when viewed in a plan view from the subject side, each of the separating regions overlap the light blocking layers, and one light receiving face of the light receiving element is positioned within each of the opening portions.

Such a configuration also has an effect that is similar to the sensing device according to the first aspect. That is, the first electrode may also be a plurality of electrodes that are provided apart from one another.

Further, the sensing device according to the third aspect may have a configuration including: a first driving circuit that selects a portion of the second electrodes out of the plurality of second electrodes as a target to supply a driving signal for causing the light emitting layer to emit light; and a reading circuit that reads a light receiving signal that indicates the light amount of the reflected light that is incident on the light receiving faces from the light receiving elements that are adjacent to a portion of the second electrodes that the first driving circuit has selected out of the plurality of light receiving elements in a case when viewed in a plan view from the subject side.

According to such a configuration, it is possible to cause irradiation light to be emitted from only the portion that corresponds to the portion of the second electrodes that the first driving circuit has selected out of the light emitting layer in a case when viewed in a plan view from the subject side. Further, the light receiving signals are able to be read from only the light receiving elements that are adjacent to the portion of the second electrodes that is the first driving circuit has selected, that is, the light receiving elements that are positioned in the vicinity of the portion to which the irradiation light is emitted out of the light emitting layer. Since driving while limiting the light emitting range of the irradiation light and the reading range of the light receiving signals is possible as a part, it is possible to reduce the power consumption of the sensing device.

Further, the sensing device described above may have a configuration including a control circuit that detects a region in which the subject is placed out of the reading region in which the image of the subject is read, and that determines the portion of the second electrodes that the first driving circuit selects based on the detection result.

In such a case, it is possible to determine the light emitting range of the irradiation light and the reading range of the light receiving signal according to the size or position of the subject that is placed in the reading region.

Further, the sensing device according to the fourth aspect may have a configuration including: a first driving circuit that selects a portion of the second electrodes out of the plurality of second electrodes as a target to supply a driving signal for causing the light emitting layer to emit light; a second driving circuit that selects a portion of the first electrodes out of the plurality of first electrodes as a target to supply the driving signal; and a reading circuit that reads a light receiving signal that indicates the light amount of the reflected light that is incident on the light receiving faces from the light receiving elements that are adjacent to a portion in which the portion of the second electrodes that the first driving circuit has selected and the portion of the first electrodes that the second driving circuit has selected overlap out of the plurality of light receiving elements in a case when viewed in a plan view from the subject side.

Even in the case of such a configuration, since driving while limiting the light emitting range of the irradiation light and the reading range of the light receiving signals is possible as a part, it is possible to reduce the power consumption of the sensing device.

Further, the sensing device described above may have a configuration including a control circuit that detects a region in which the subject is placed out of the reading region in which the subject of an image is read, and that determines the portion of the second electrodes that the first driving circuit has selected and the portion of the first electrodes that the second driving circuit selects based on the detection result.

Even in such a case, it is possible to determine the light emitting range of the irradiation light and the reading range of the light receiving signal according to the size or position of the subject that is placed in the reading region.

Further, the sensing device according to the third aspect may have a configuration including: a first driving circuit that selects one or more second electrodes out of the plurality of second electrodes as targets to supply a driving signal for causing the light emitting layer to emit light; a reading circuit that reads a light receiving signal that indicates the light amount of the reflected light that is incident on the light receiving faces from each of the plurality of light receiving elements; and a generation circuit that generates an image that is the subject based on the light receiving signal that the reading circuit reads; wherein the plurality of second electrodes are divided into a plurality of groups, the first driving circuit sequentially selects the plurality of second electrodes in units of the groups, the reading circuit reads the light receiving signals from all of the light receiving elements every time that the first driving circuit performs selection in units of the groups, and the generation circuit excludes at least the light receiving signals that are read from the light receiving elements that are adjacent to the one or more second electrodes that the first driving circuit has selected in a case when viewed in a plan view from the subject side and generates an image of the subject based on the remaining light receiving signals from all of the light receiving signals that the reading circuit reads every time that the first driving circuit performs selection in units of the groups.

According to such a configuration, it is possible to generate an image of the subject without using the light receiving signals from the light receiving elements that are adjacent to the one or more second electrodes that the first driving circuit has selected, that is, the light receiving signals from the light receiving elements that are positioned in the vicinity of the portions to which the irradiation light is emitted out of the light emitting layer in a case when viewed in a plan view from the subject side. It is therefore possible to prevent the image quality of the vein image from decreasing due to the surface reflected light that reflects off the surface of the living body (skin) in a case when a vein image is generated from the light receiving result of the reflected light by irradiating near-infrared light on a portion of a living body.

Further, the sensing device according to the third aspect may have a configuration including: a first driving circuit that selects one or more second electrodes out of the plurality of second electrodes as targets to supply a driving signal for causing the light emitting layer to emit light; a reading circuit that reads a light receiving signal that indicates the light amount of the reflected light that is incident on the light receiving faces from each of the plurality of light receiving elements; and a generation circuit that generates an image of the subject based on the light receiving signal that the reading circuit has read, wherein the plurality of second electrodes are divided into a plurality of groups, the first driving circuit sequentially selects the plurality of second electrodes in units of the groups, and the reading circuit excludes at least the light receiving elements that are adjacent to the one or more second electrodes that the first driving circuit has selected in a case when viewed in a plan view from the subject side and reads the light receiving signals from the remaining light receiving elements every time that the first driving circuit performs selection in units of the groups.

Even in such a case, it is possible to generate an image of the subject without using the light receiving signals from the light receiving elements that are positioned in the vicinity of the portions to which the irradiation light is emitted out of the light emitting layer. It is therefore possible to prevent the image quality of the vein image from decreasing due to the surface reflected light in a case when a vein image is generated using near-infrared light as the irradiation light or the reflected light. Further, since it is not necessary to read the light receiving signals from the light receiving elements on which the surface reflected light is incident, it is also possible to decrease the power consumption of the sensing device.

Further, the sensing device according to the fourth aspect may have a configuration including: a first driving circuit that selects one or more second electrodes out of the plurality of second electrodes as targets to supply a driving signal; a second driving circuit that selects one or more first electrodes out of the plurality of first electrodes as targets to supply a driving signal; a reading circuit that reads a light receiving signal that indicates the light amount of the reflected light that is incident on the light receiving faces from each of the plurality of light receiving elements; and a generation circuit that generates an image of the subject based on the light receiving signal that the reading circuit has read, wherein the plurality of first electrodes and the plurality of second electrodes are divided into a plurality of groups, the first driving circuit sequentially selects the plurality of second electrodes in units of the groups, the second driving circuit sequentially selects the plurality of first electrodes in units of the groups, the reading circuit reads the light receiving signals from all of the light receiving elements every time that the first driving circuit and the second driving circuit perform selection in units of the groups, and the generation circuit excludes at least the light receiving signal that is read from the light receiving element that is closest to a portion in which the one or more second electrodes that the first driving circuit has selected and the one or more first electrodes that the second driving circuit has selected overlap in a case when viewed in a plan view from the subject side and generates an image of the subject based on the remaining light receiving signals every time that the first driving circuit and the second driving circuit perform selection in units of the groups.

Even with such a configuration, it is possible to generate an image of the subject without using the light receiving signal from the light receiving element that is closest to a portion in which the one or more second electrodes that the first driving circuit has selected and the one or more first electrodes that the second driving circuit has selected overlap, that is, without using the light receiving signal from the light receiving element that is closest to the portions to which the irradiation light is emitted out of the light emitting layer. It is therefore possible to prevent the image quality of the vein image from decreasing due to the surface reflected light in a case when a vein image is generated using near-infrared light as the irradiation light or the reflected light.

Further, the sensing device according to the fourth aspect may have a configuration including: a first driving circuit that selects one or more second electrodes out of the plurality of second electrodes as targets to supply a driving signal; a second driving circuit that selects one or more first electrodes out of the plurality of first electrodes as targets to supply a driving signal; a reading circuit that reads the light receiving signal that indicates a light amount of the reflected light that is incident on the light receiving faces from each of the plurality of light receiving elements; and a generation circuit that generates an image of the subject based on the light receiving signal that the reading circuit has read, wherein the plurality of first electrodes and the plurality of second electrodes are divided into a plurality of groups, the first driving circuit sequentially selects the plurality of second electrodes in units of the groups, the second driving circuit sequentially selects the plurality of first electrodes in units of the groups, and the reading circuit excludes at least the light receiving element that is closest to a portion in which the one or more second electrodes that the first driving circuit has selected and the one or more first electrodes that the second driving circuit has selected overlap in a case when viewed in a plan view from the subject side and reads the light receiving signals from the remaining light receiving elements every time that the first driving circuit and the second driving circuit perform selection in units of the groups.

Even in such a case, it is possible to generate an image of the subject without using the light receiving signals from the light receiving elements that are positioned in the vicinity of the portions to which the irradiation light is emitted, out of the light emitting layer. It is therefore possible to prevent the image quality of the vein image from decreasing due to the surface reflected light in a case when a vein image is generated using near-infrared light as the irradiation light or the reflected light. Further, since it is not necessary to read the light receiving signals from the light receiving elements on which surface reflected light is incident, it is also possible to reduce the power consumption of the sensing device.

Further, according to any of the sensing devices described above, the light emitting layer may have a configuration of emitting near-infrared light. That is, the irradiation light or the reflected light may be near-infrared light. In such a case, a vein image can be generated by irradiating near-infrared light on a portion of a living body and receiving the reflected light.

Further, an electronic apparatus according to the invention includes any of the sensing devices described above. Other than various biometric authentication devices that perform biometric authentication based on, for example, veins, fingerprints, retinas, irises, and the like, the electronic apparatus includes image reading devices such as image scanners, photocopiers, facsimiles, and barcode readers. Further, the electronic apparatus may be a personal computer, a mobile phone, or the like that includes a biometric authentication function.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
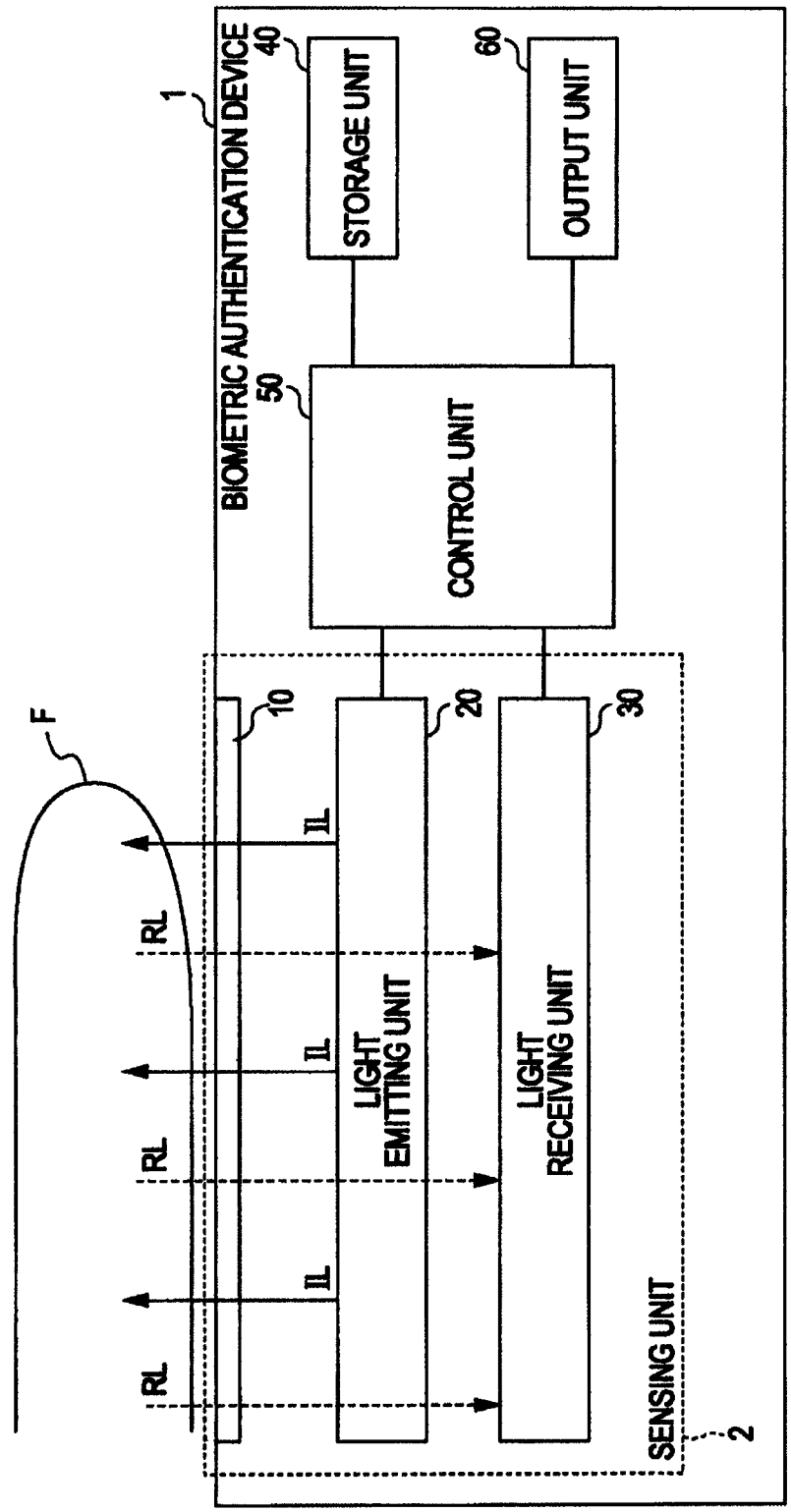
FIG. 1 is a block diagram that illustrates a configuration of a biometric authentication device according to the first aspect.

Aspects according to the invention will be described below with reference to the drawings. Here, the proportions of the dimensions of each of the layers and members in the drawings differ from reality as appropriate.

A. FIRST ASPECT

FIG. 1 is a block diagram that illustrates a configuration of a biometric authentication device 1 according to a first aspect.

The biometric authentication device 1 illustrated in the drawing is a device that performs personal authentication by capturing a vein image of a finger F, and includes a sensing unit 2, a storage unit 40, a control unit 50, and an output unit 60. Further, the sensing unit 2 includes a cover glass 10, a light emitting unit 20, and a light receiving unit 30. The cover glass 10 is a glass protective cover that covers the capturing region. The finger F (for example, the right index finger) of the person that is the authentication target is placed on the cover glass 10. The light emitting unit 20 includes, for example, a light emitting layer formed by an organic EL (Electro Luminescent) material, an anode, a cathode, and an insulating layer, and emits irradiation light IL that irradiates the finger F. The irradiation light IL is near-infrared light, and the wavelength thereof is, for example, 750 nm to 3000 nm (more preferably 800 nm to 900 nm).

The irradiation light IL (near-infrared light) that exits the light emitting unit 20 irradiates the finger F from the lower side of the cover glass 10, scatters when the irradiation light reaches the inside of the finger F, and a portion thereof heads toward the light receiving unit 30 side as reflected light (RL). The reduced hemoglobins that flow through veins have a property of absorbing near-infrared light. Therefore, if the finger F is captured using a near-infrared image sensor, the vein portions below the skin of the finger F appear dark compared to the surrounding tissue. The pattern due to the differences in lightness becomes a vein image. The light receiving unit 30 is a near-infrared image sensor, and includes a plurality of light receiving elements that are arranged in a matrix pattern. Each light receiving element converts incident light (the reflected light RL from the finger F) into an electrical signal (light receiving signal) with a signal level according to the light amount of the incident light.

Here, while specific structures of the light emitting unit 20 and the light receiving unit 30 will be described later, as illustrated in FIG. 1, the light emitting unit 20 and the light receiving unit 30 are positioned on the same side with regard to the finger F that is placed on the cover glass 10 (lower side in the drawing). Further, the light emitting unit 20 is positioned further to the cover glass 10 side (upper side in the drawing) than the light receiving unit 30.

The storage unit 40 is a non-volatile memory such as a flash memory or a hard disk, and a vein image of the finger F (for example, the right index finger) that is registered in advance is stored therein as a master vein image for personal authentication. The control unit 50 includes a CPU (Central Processing Unit) or a RAM (Random Access Memory), and controls the lighting or the switching off of the light emitting unit 20. Further, the control unit 50 reads the light receiving signal from each light receiving element that is included in the light receiving unit 30, and generates a vein image of the finger F based on the light receiving signals for one frame (for the capturing region) that is read. Further, the control unit 50 performs personal authentication by collating the generated vein image with the master vein image that is recorded in the storage unit 40. For example, the control unit 50 compares the characteristics of the two vein image that are collated (for example, the number and positions of branches of veins, or the like), and in a case when the similarity is equal to or greater than a threshold value set in advance, authenticates the person who has placed the finger F on the cover glass 10 as the person for whom the master vein image is registered in the storage unit 40. The output unit 60 is, for example, a display unit or a sound notification unit, and notifies of the authentication result using a display or a sound.

Figure 2:
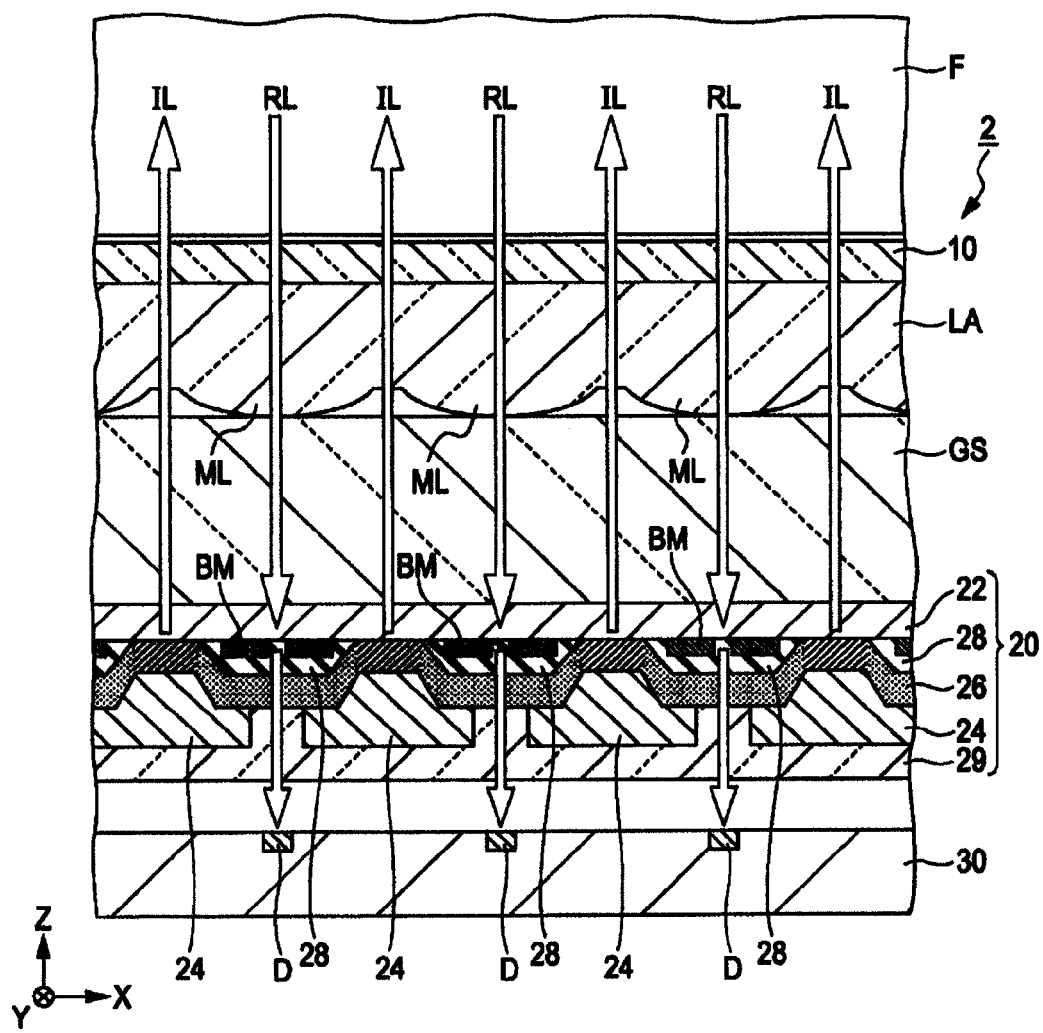
FIG. 2 is a cross-sectional diagram of a sensing unit.

FIG. 2 is a cross-sectional diagram of a sensing unit 2.

In the drawing, a plurality of light receiving elements D are arranged on the upper face of the light receiving unit 30 (near-infrared image sensor) in a matrix pattern. Each light receiving element D converts the reflected light RL (near-infrared light) that is incident on a light receiving face into a light receiving signal with a signal level according to the light amount of the reflected light RL. Further, an opposing substrate GS that is arranged to be opposing on the upper side of the light receiving unit 30 is formed by a material with high transmittance with respect to near-infrared light such as, for example, clear glass or clear plastic. A lens array LA and the cover glass 10 are provided on the upper side of the opposing substrate GS across the entire face of the capturing region. The lens array LA and the cover glass 10 are formed by a material with high transmittance with respect to near-infrared light. The lens array LA is an arrangement of a plurality of micro lenses ML in a matrix pattern. The arrangement pitch of the micro lenses ML is the same as the arrangement pitch of the light receiving elements D, and each micro lens ML images the reflected light RL from the finger F onto the light receiving face of a light receiving element D that is positioned directly below.

Figure 3:
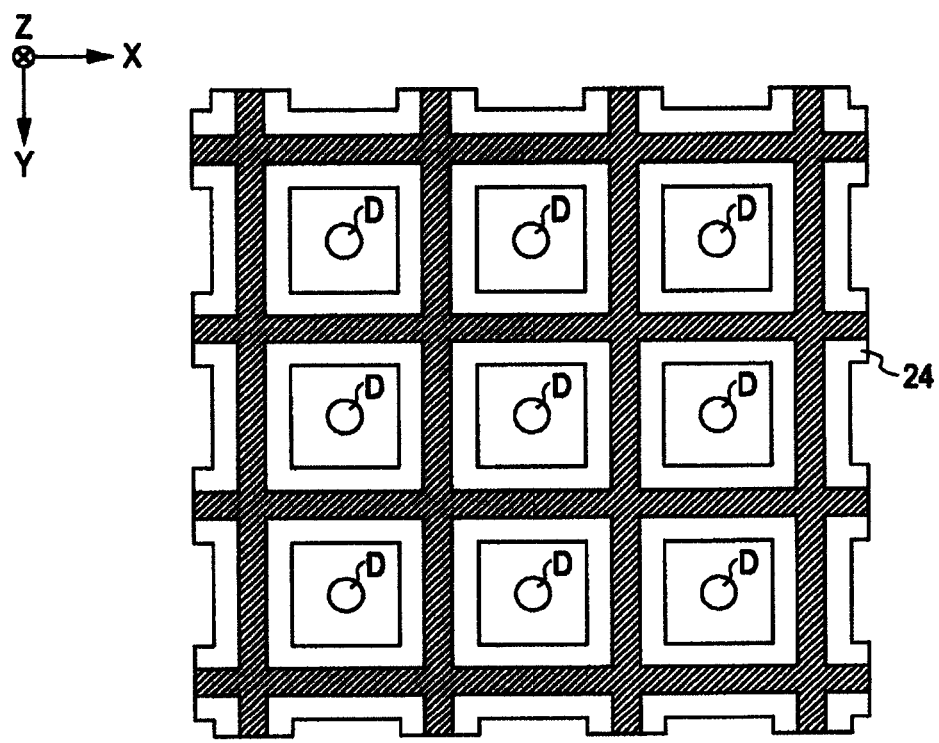
FIG. 3 is a plan diagram that illustrates an arrangement of a cathode and light receiving elements.

On the other hand, a light emitting unit 20 and a plurality of light blocking layers BM are provided on the lower side of the opposing substrate GS. First, an anode 22 is formed across the entire face of the capturing region on the lower face of the opposing substrate GS. The anode 22 is a film-like electrode (conductor) that opposes a cathode 24 with an organic EL layer 26 (or the light blocking layers BM, an insulating layer 28, and the organic El layer 26) interposed therebetween, and is formed by a material with high transmittance with respect to near-infrared light and with high conductivity. On the other hand, the cathode 24 is an electrode (conductor) on which opening portions are provided at positions that correspond to each of the plurality of light receiving elements D, and is formed by a material with a high light blocking property and high conductivity. Further, the lower side of the cathode 24 or each opening portion of the cathode 24 is covered by a sealing layer 29 that is formed by a material with high transmittance with respect to near-infrared light. Here, FIG. 3 is a plan view that illustrates the arrangement of the cathode 24 and the light receiving elements D. As illustrated in the drawing, the shape of each opening portion that is provided on the cathode 24 is a square, and the cathode 24 has a #-like shape when viewed in a plan view from the cover glass 10 side. The arrangement pitch of the opening portions is the same as the arrangement pitch of the light receiving elements D, and the opening portions and the light receiving elements D (light receiving faces) are in a one-to-one correspondence. Further, one light receiving element D (light receiving face) is included in each opening portion. Here, the cathode 24 may be configured by a transparent electrode and light blocking layers. That is, the cathode 24 may be configured by overlapping a #-shaped transparent electrode that is formed by a material with high transmittance with respect to near-infrared light and with high conductivity and #-shaped light blocking layers that are formed by a material with a high light blocking property with respect to near-infrared light.

Returning to FIG. 2, a light blocking layer BM is provided at a position that corresponds to each opening portion that is provided on the cathode 24 on the lower face of the anode 22. Each light blocking layer BM is formed by a material with a high light blocking property with respect to near-infrared light, and an opening portion is provided at a position that corresponds to the light receiving face of the light receiving element D. Each light blocking layer BM (each opening portion) causes the reflected light RL that has transmitted the micro lens ML that is positioned directly above to be incident on the light receiving face of the light receiving element D that is positioned directly below.

Further, each of the light blocking layers BM are covered by the insulating layer 28 for each light blocking layer BM. Each insulating layer 28 is formed by a material with high transmittance with respect to near-infrared light and with high insulating properties. Each insulating layer 28 partially insulates the anode 22 and the cathode 24 and forms a non-light emitting region in which near-infrared light is not emitted to the organic EL layer 26. Here, since each insulating layer 28 is provided at a position that corresponds to each of the opening portions of the cathode 24, the positions corresponding to the light receiving faces of each of the light receiving element D and the vicinity thereof out of the organic EL layer 26 are the non-light emitting region. That is, there is no light emitting region in which near-infrared light is emitted out of the organic EL layer 26 on the light path of the reflected light RL which is incident on the light receiving face of each light receiving element D (on a straight line that extends from the light receiving face of each light receiving element D in the Z axis direction).

The organic EL layer 26 is a light emitting layer that is formed by an organic EL material with high transmittance with respect to near-infrared light, and is formed over the entire face of the capturing region. The organic EL layer 26 emits near-infrared light by positive holes and electrons being coupled by supplying an electric current. Further, while the organic EL layer 26 emits light from a portion between the anode 22 and the cathode 24, since the portion on which the insulating layer 28 is formed insulates the anode 22 and the cathode 24, as illustrated in FIG. 2, the portions indicated by the hatching out of the organic EL layer 26 (portions that are directly interposed between the anodes 22 and the cathodes 24) become the light emitting regions that emit near-infrared light and other portions become the non-light emitting regions. In such a manner, there are light emitting regions and non-light emitting regions in the organic EL layer 26.

Here, the light emitting regions of the organic EL layer 26 are the portions indicated by the hatching in FIG. 3 when viewed in a plan view from the cover glass 10 side. Since the light emitting regions illustrated in the drawing are formed to surround the vicinity of each light receiving element D, near-infrared, light (irradiation light IR) of even strength can be irradiated on the finger F.

Figure 4:
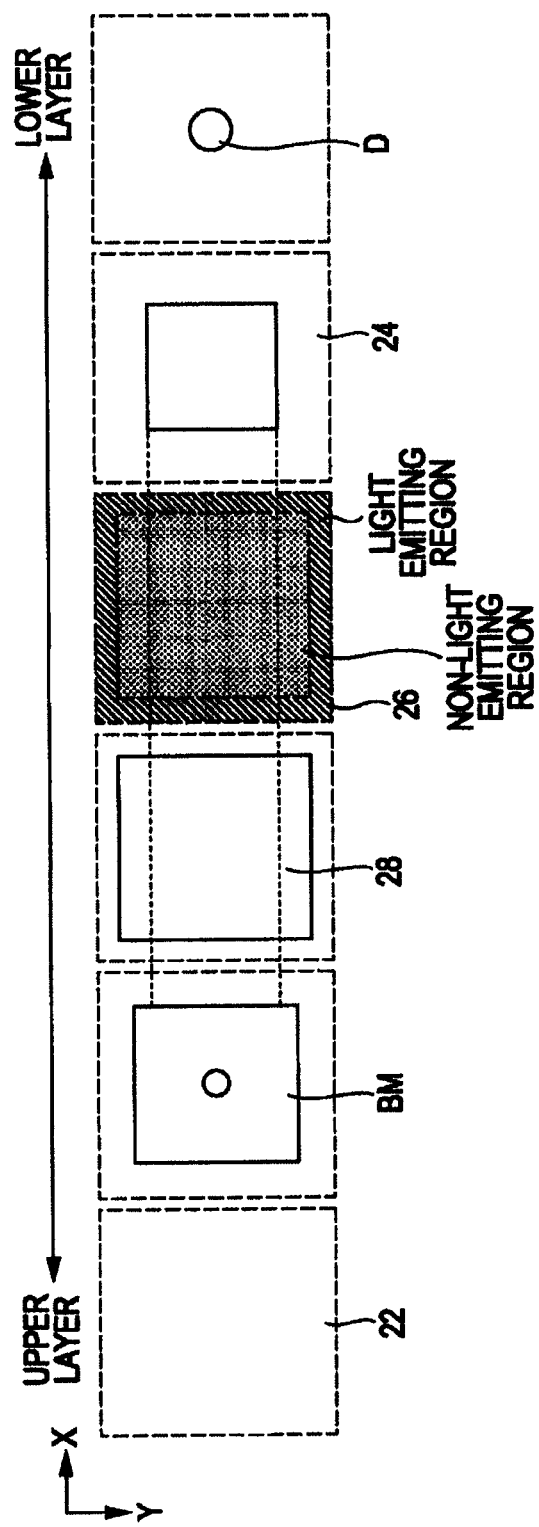
FIG. 4 is a schematic diagram that illustrates the arrangement of each layer in a case when one light receiving element is observed.

FIG. 4 is a schematic diagram that illustrates the arrangement of each layer in a case when one light receiving element D is observed.

The light receiving face of the light receiving element D that is positioned on the lowermost layer in the drawing has a circular shape. Further, the cathode 24 with a square opening portion that is larger than the light receiving face of the light receiving element D is provided thereabove. On the other hand, the anode 22 is provided across the entire face of the uppermost layer, and the light blocking member BM with a square external shape that is larger than the opening portion of the cathode 24 is provided thereunder. A circular opening portion that is smaller than the light receiving face of the light receiving element D is provided at the center of the light blocking layer BM, and portions other than such an opening portion are blocked by the light blocking layer BM and the cathode 24. In such a manner, the light blocking layer BM and the cathode 24 cover portions other than the opening portion of the light blocking layer BM when viewed in a plan view from the cover glass 10 side, and function as a light receiving window of the light receiving element D. Further, the insulating layer 28 is formed under the light blocking layer BM.

The insulating layer 28 has a larger external shape (square) than the light blocking layer BM and covers the entire face of the light blocking layer BM. Further, the organic EL layer 26 is provided over the entire face below the insulating layer 28. Portions of the organic EL layer 26 which are interposed between the anode 22 and the cathode 24 and which are not insulated by the insulating layer 28 emit light. Therefore, the surrounding portions indicated by the hatching out of the organic EL layer 26 illustrated in the drawing become the light emitting regions, and the inner side portions thereof become the non-light emitting regions.

As is also clear from FIG. 4, the position that corresponds to the light receiving face of the light receiving elements D and the surroundings thereof out of the organic EL layer 26 become the non-light emitting region. Therefore, there are no light emitting regions that emit irradiation light IL with a greater light amount than the reflected light RL on the light path of the reflected light that is incident on the light receiving face of the light receiving element D. Further, since portions other than the opening portion of the light blocking layer BM are blocked by the light blocking layer BM and the cathode 24, the reflected light RL that has transmitted through the micro lens ML that is positioned directly above is incident on the light receiving face of the light receiving element D, and the reflected light RL (scattered light) that is incident diagonally from adjacent micro lenses ML and the like being incident on the light receiving face of the light receiving element D can be suppressed.

Next, the actions of the biometric authentication device 1 will be described.

Once the control unit 50 detects that the finger F has been placed on the cover glass 10 using a contact sensor or the like (not shown), the control unit 50 supplies an electric current between the anode 22 and the cathode 24 and causes the organic EL layer 26 (light emitting region) to emit light. The irradiation light IL (near-infrared light) that exits from the organic EL layer 26 is irradiated on the finger F via the anode 22, the opposing substrate GS, the lens array LA, and the cover glass 10, scatters when the irradiation light IL reaches the inside of the finger F, and a portion thereof heads toward the light receiving unit 30 side as reflected light RL. Further, a portion of the reflected light RL from the finger F is incident on the light receiving face of a light receiving elements D via the cover glass 10, the lens array LA, the opposing substrate GS, the anode 22, the opening portion of the light blocking layer BM, the insulating layer 28, the organic EL layer 26 (non-light emitting region), the opening portion of the cathode 24, and the sealing layer 29. Each light receiving element D converts the reflected light RL that is incident on the light receiving face into a light receiving signal with a signal level according to the light amount thereof. The control unit 50 reads the light receiving signal from each light receiving element D and generates a vein image of the finger F based on the light receiving signals for one frame which is read. Further, the control unit 50 performs personal authentication by collating the generated vein image with the master vein image that is registered in the storage unit 40 and outputs the authentication result from the output unit 60.

According to the aspect described above, the positions that correspond to the light receiving faces of each of the light receiving elements D out of the organic EL layer 26 and the surroundings thereof become the non-light emitting regions. There are therefore no light emitting regions that emit irradiation light IL with a greater light amount than the reflected light RL on the light path of the reflected light RL that is incident on the light receiving face of each light receiving element D. Further, portions other than the opening portion of each light blocking layer BM are blocked by each light blocking layer BM and the cathode 24. The reflected light RL that has transmitted the micro lens ML that is portioned directly above is therefore incident on the light receiving face of each light receiving element D, and it is possible to suppress the incidence of the reflected light RL (scattered light) that is incident diagonally from adjacent micro lenses ML or the like. Further, it is also possible to suppress the irradiation light IL that exits from the organic EL layer 26 (light emitting region) from passing through the opening portion of the cathode 24 and being directly incident on the light receiving face of each light receiving element D by the cathode 24 and each light blocking layer BM. Accordingly, since it is possible to receive the reflected light from the finger F by each light receiving element D with high precision, it is possible to increase the capturing precision of the vein image. Further, although it is necessary to provide the anodes 22, the cathodes 24, the organic EL layer 26, the insulating layers 28, and the light blocking layers BM, since each such element can be formed to be extremely thin, compared to the invention described in JP-A-2009-172263, the thickness of the biometric authentication device 1 (sensing unit 2) in the Z axis direction can be made thin.

B. SECOND ASPECT

Figure 5:
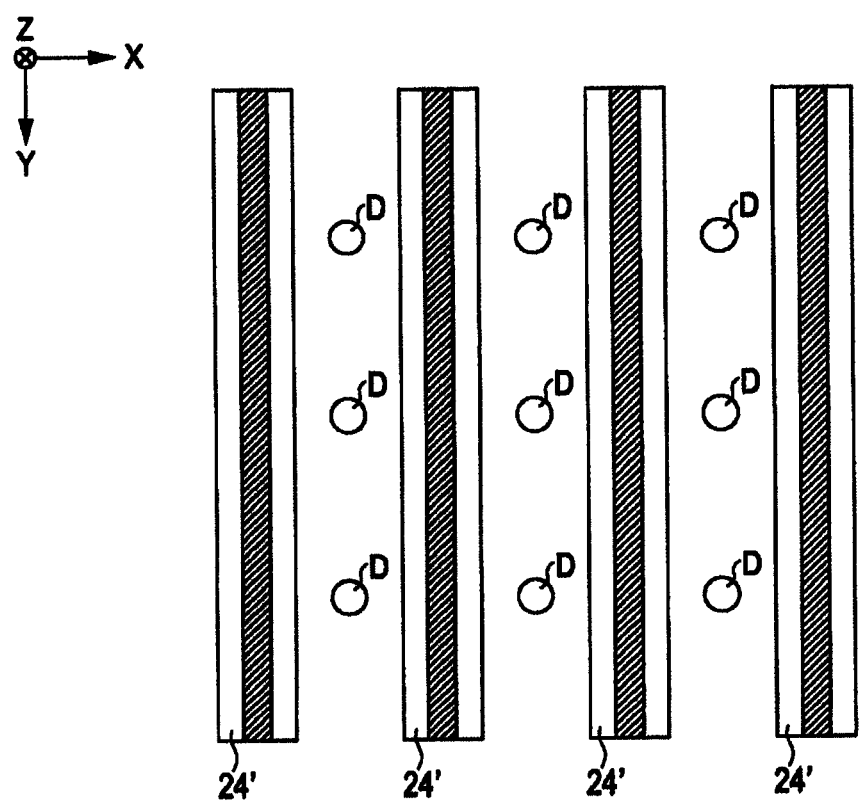
FIG. 5 is a plan diagram that illustrates an arrangement of cathodes and light receiving elements according to a second aspect.

One cathode 24 (FIG. 3) with a plurality of opening portions according to the first aspect described above may be a plurality of cathodes 24' that are arranged apart from one another as illustrated in FIG. 5. Each of the cathodes 24' has a strip-like shape that extends in the Y axis direction, and is arranged apart from one another to avoid overlapping with the plurality of light receiving elements D that are included in the light receiving unit 30. In such a case, each light blocking layer BM and each insulating layer 28 according to the first aspect must also change the external shape or the like thereof so as to cover the separating regions between adjacent cathodes 24' in FIG. 5.

Figure 6:
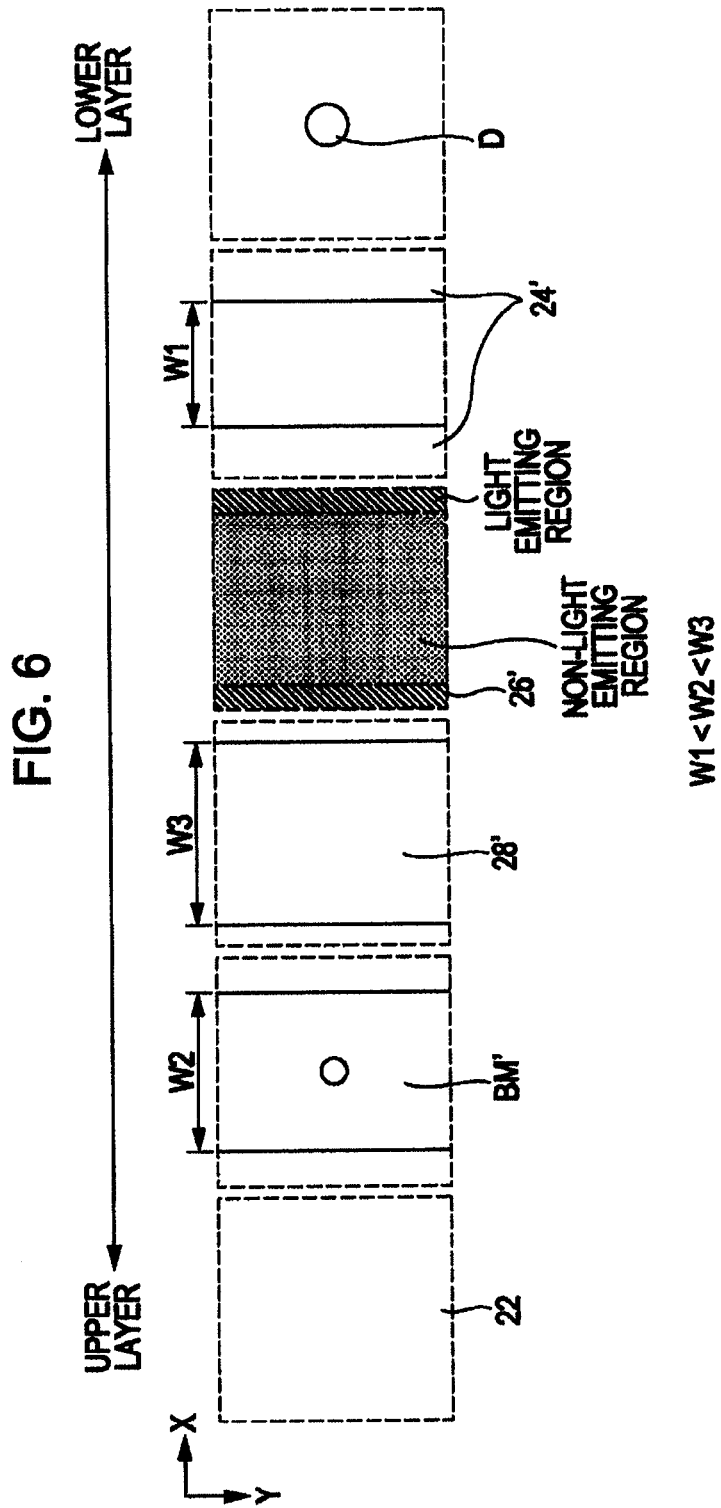
FIG. 6 is a schematic diagram that illustrates the arrangement of each layer in a case when one light receiving element is observed.

FIG. 6 is a schematic diagram that illustrates the arrangement of each layer according to the second aspect.

Here, the light receiving element D and the anode 22 are the same as those described in the first aspect. As illustrated in the drawing, the two cathodes 24' that extend in the Y direction are positioned on both sides (left and right in the drawing) of the light receiving element D with the light receiving face thereof interposed therebetween. When the width of the interval between the two cathodes 24' is W1, a width W2 of a light blocking layer BM' in the X axis direction is greater than W1. The light blocking layer BM' has a strip-like external shape that extends in the Y axis direction. Further, the light blocking layer BM' has a circular opening portion that is smaller than the light receiving face at a position that corresponds to the light receiving face of the light receiving element D. Here, as illustrated in FIG. 5, since a plurality of light receiving elements D are arranged along the Y axis direction, a plurality of opening portions are also formed on each light blocking layer BM' along the Y axis direction.

Further, a width W3 of an insulating layer 28' in the X axis direction is greater than the width W2 of the light blocking layer BM'. The insulating layer 28' also has a strip-like external shape that extends in the Y axis direction similarly to the light blocking layer BM'. The insulating layer 28' and the light blocking layer BM' cover the separating region between the two cathodes 24', and both ends (X axis direction) of the insulating layer 28' and the light blocking layer BM' overlap the cathodes 24' at both ends. Further, while an organic EL layer 26' is distributed across the entire face, portions that are interposed between an anode 22' and the cathodes 24' and that are not insulated by the insulating layer 28' emit light. Therefore, as illustrated in the drawing, both side portions indicated by the hatching out of the organic EL layer 26' become the light emitting regions, and the inner side portion thereof becomes the non-light emitting region. Here, according to the present aspect, an electric current is supplied to the plurality of cathodes 24' at the same time. Therefore, the light emitting regions of the organic EL layer 26' are the portions indicated by the hatching in FIG. 5 when viewed in a plan view from the cover glass 10 side.

Even with the configuration described above, the positions that correspond to the light receiving faces of each of the light receiving elements D and the vicinity thereof out of the organic EL layer 26' become the non-light emitting regions. There are therefore no light emitting regions that emit the irradiation light IL with a greater light amount than the reflected light RL on the light path of the reflected light RL that is incident on the light receiving face of each light receiving element D. Further, portions other than the opening portions of the light blocking layer BM' are blocked by the light blocking BM' and the two cathodes 24' on both sides thereof. Therefore, the reflected light RL that has transmitted through the micro lens ML that is positioned directly above is incident on the light receiving face of each light receiving element D. The same effects as the first aspect are thereby obtained.

C. THIRD ASPECT

Figure 7:
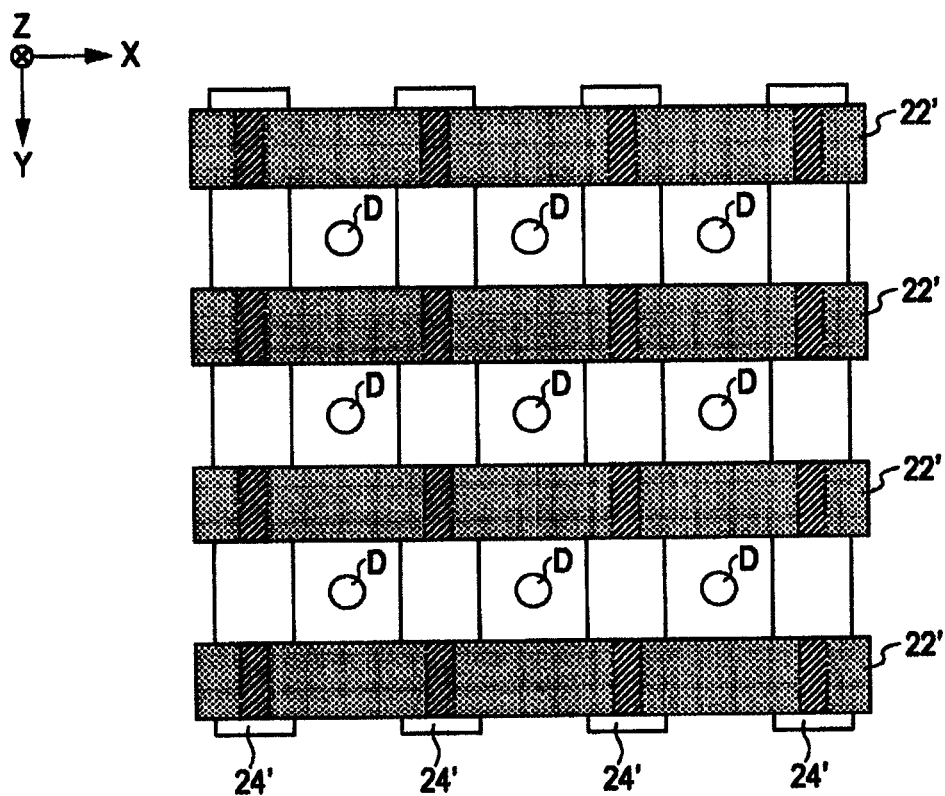
FIG. 7 is a plan diagram that illustrates an arrangement of anodes, cathodes, and light receiving elements according to a third aspect.

In addition to the cathode 24, the anode 22 according to the first aspect described above may also be a plurality of anodes 22' that are arranged apart from one another as illustrated in FIG. 7. Each of the anodes 22' has a strip-like shape that extends in the X axis direction, and are arranged apart from one another so as to avoid overlapping with the plurality of light receiving elements D that are included in the light receiving unit 30.

Figure 8:
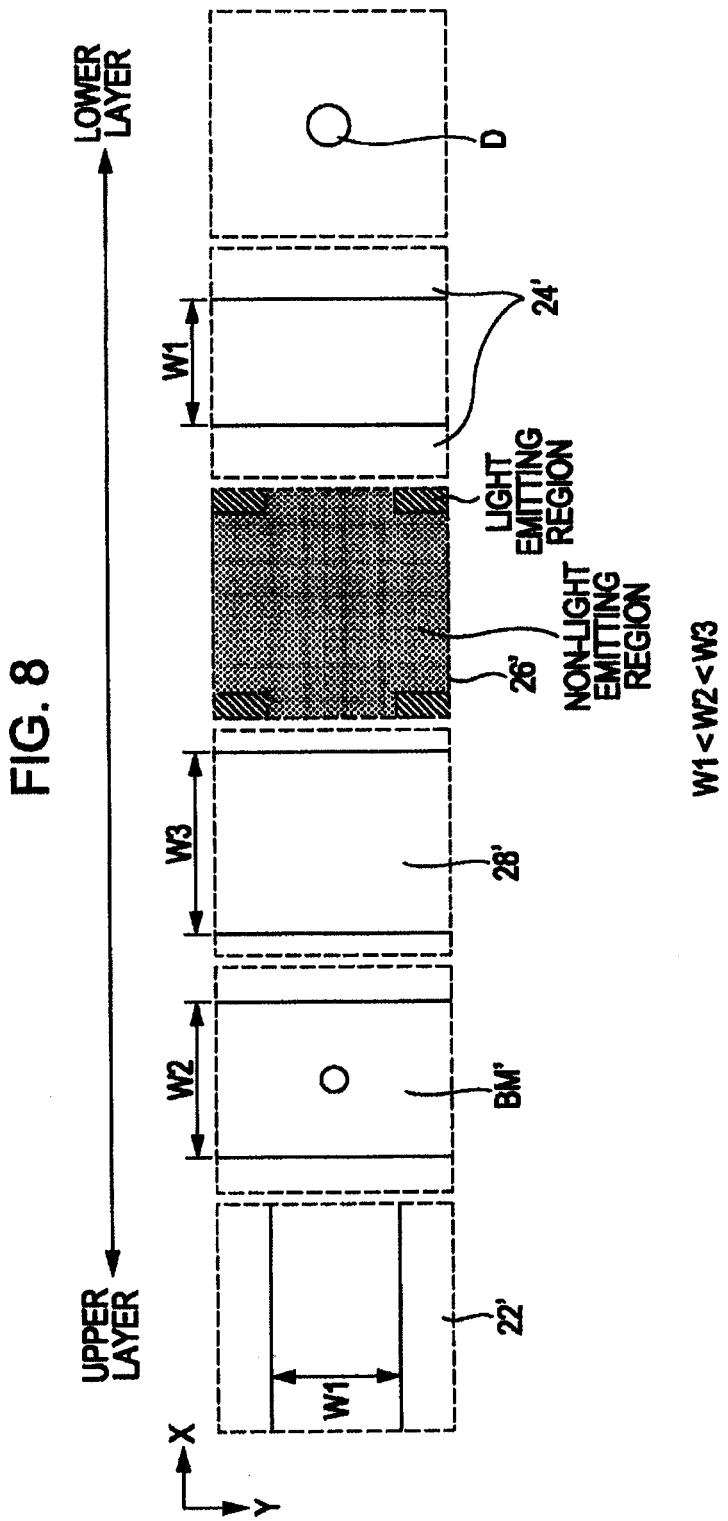
FIG. 8 is a schematic diagram that illustrates the arrangement of each layer in a case when one light receiving element is observed.

FIG. 8 is a schematic diagram that illustrates the arrangement of each layer according to the third aspect.

Here, the light blocking layers BM', the insulating layers 28', the cathodes 24', and the light receiving elements D are the same as those described in the second aspect. As illustrated in the drawing, the two anodes 22' that extend in the X axis direction are positioned on both ends (up and down in the drawing) of a light receiving element D with the light receiving face thereof interposed therebetween. Further, the width of the interval between the anodes 22' is the same W1 as the width of the interval between the cathodes 24'. While the organic EL layer 26' is distributed across the entire face, portions that are interposed between the anodes 22' and the cathodes 24' and that are not insulated by the insulating layer 28' emit light. Therefore, as illustrated in the drawing, the portions of the four corners that are indicated by the hatching out of the organic EL layer 26' become the light emitting regions, and other portions become the non-light emitting region. Here, according to the present aspect, an electric current is supplied to the plurality of anodes 22' and the plurality of cathodes 24' at the same time. Therefore, the light emitting regions of the organic EL layer 26' are the portions indicated by the hatching in FIG. 7 when viewed in a plan view from the cover glass 10 side.

Even with such a configuration, the positions that correspond to the light receiving faces of each of the light receiving elements D and the vicinity thereof out of the organic EL layer 26' become the non-light emitting regions. Further, the portions other than the opening portions of a light emitting layer BM' are blocked by the light blocking layer BM' and the two cathodes 24' on both sides thereof. The same effects as the first aspects are thereby obtained.

D. FOURTH ASPECT

Incidentally, light that has reflected off the surface (skin) of the finger F is included in the reflected light RL that is incident on the light receiving face of each light receiving element D. Such surface reflected light decreases the capturing precision of the vein image. Therefore, in the present aspect, a biometric authentication device that can prevent a decrease in the capturing precision due to surface reflected light will be described.

Figure 9:
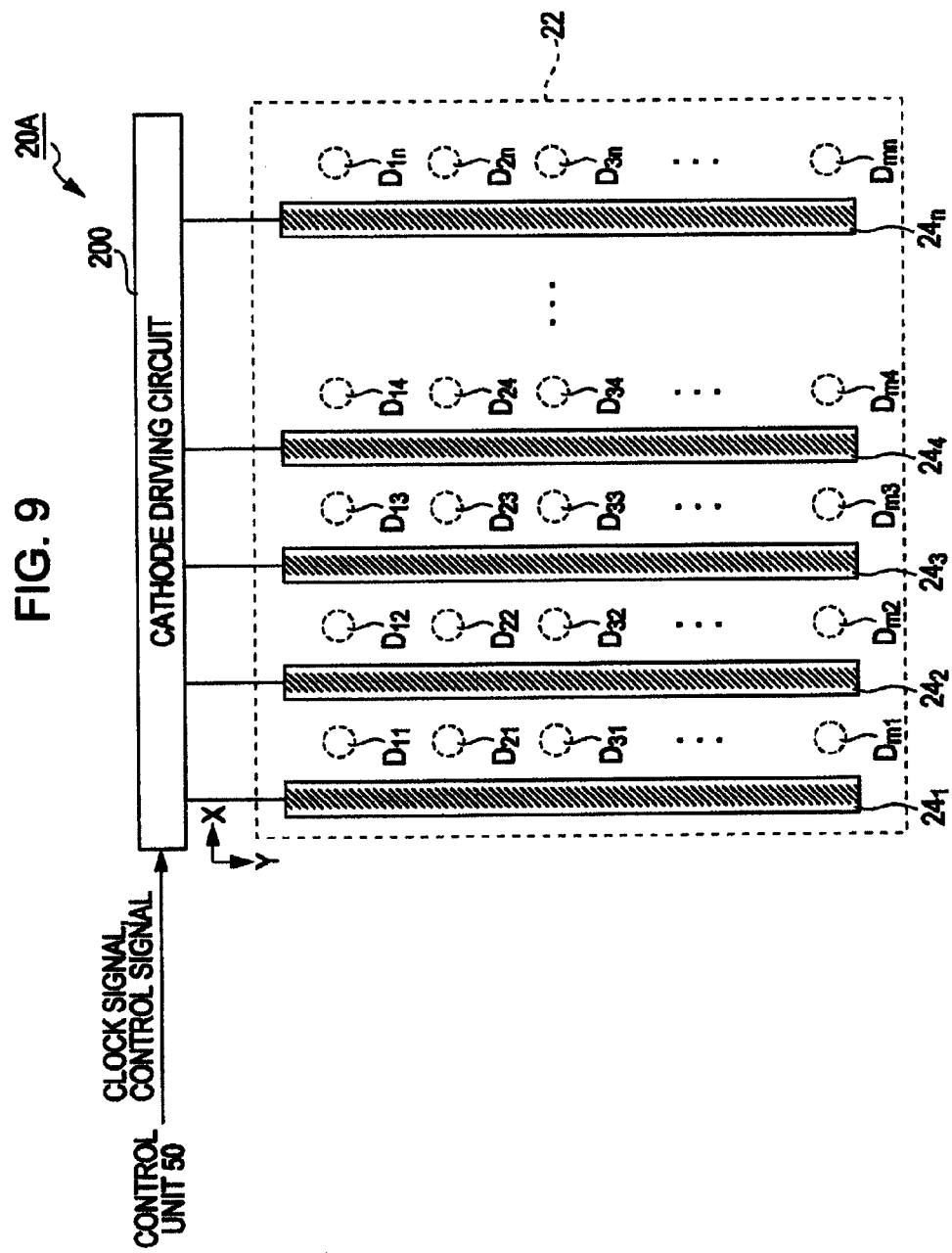
FIG. 9 is a diagram that illustrates a circuit configuration of a light emitting unit of a biometric authentication device according to a fourth aspect.

FIG. 9 is a diagram that illustrates a circuit configuration of a light emitting unit 20A of a biometric authentication device according to a fourth aspect.

As illustrated in the drawing, an anode 22 that covers the entire face of the capturing region and n cathodes $24_1$ to $24_n$ that extend in the Y axis direction are provided on the light emitting unit 20A. Here, in a case when there of no particular need to distinguish between each of the cathodes in the description below, the cathodes will be described as cathodes 24. Further, according to the present aspect, the arrangement of the anode 22, the plurality of cathodes 24, the organic EL layer 26, the plurality of insulating layers 28, and the plurality of light blocking layers BM is the same as the second aspect described above. Further, a cathode driving circuit 200 is provided on the light emitting unit 20A. The cathode driving circuit 200 successively selects one or a plurality of cathodes 24 to which an electric current is to be supplied from the n cathodes $24_1$ to $24_n$ according to a clock signal and a control signal that are supplied from the control unit 50. That is, the organic EL layer 26 emits light by an electric current being supplied between one or more cathodes 24 that are selected by the cathode driving circuit 200 and the anode 22. For example, in a case when the cathode driving circuit 200 selects all of the cathodes $24_1$ to $24_n$, the light emitting regions of the organic EL layer 26 become the portions indicated by the hatching in the drawing.

Figure 10:
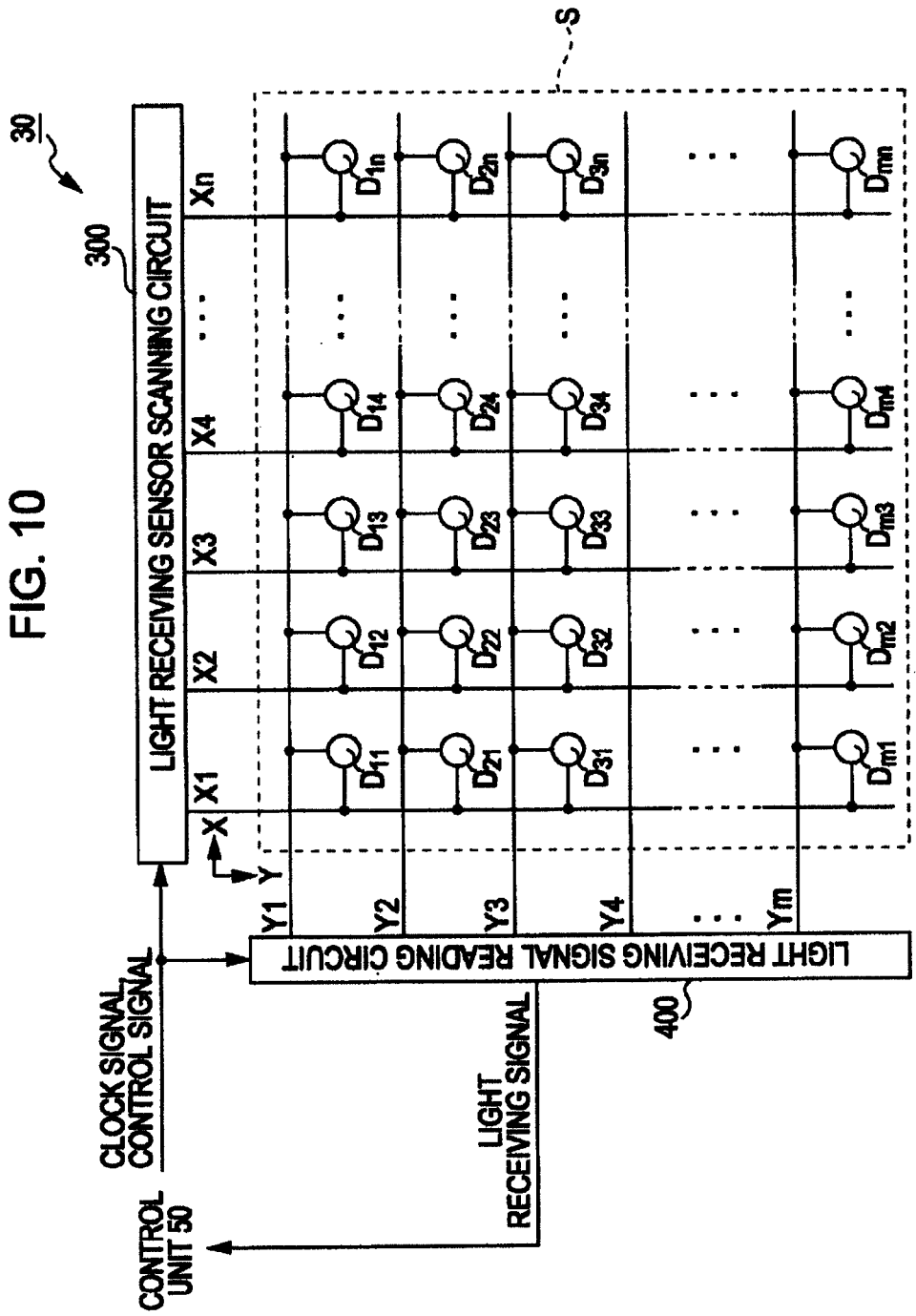
FIG. 10 is a diagram that illustrates the circuit configuration of a light emitting unit.

FIG. 10 is a diagram that illustrates a circuit configuration of a light receiving unit 30.

As illustrated in the drawing, n scan lines that extend in the Y direction and m reading lines that extend in the X direction are formed in a capturing region S, and m (rows)×n (columns) light receiving elements $D_{11}$ to $D_{mn}$ are arranged to correspond to the intersections between the scan lines and the reading lines. Here, in a case when it is not particularly necessary to distinguish between each of the light receiving elements in the description below, the light receiving elements are referred to as light receiving elements D. The control unit 50 supplies a clock signal and a control signal for scanning to a light receiving sensor scanning circuit 300. Further, the control unit 50 supplies a clock signal and a control signal for reading control to the light receiving signal reading circuit 400. The light receiving sensor scanning circuit 300 successively selects m×n light receiving elements D that are arranged in a matrix pattern using scan signals X1 to Xn. Further, the light receiving signal reading circuit 400 reads light receiving signals Y1 to Ym via m reading line from the light receiving elements D for one row (m) which are successively selected by the light receiving sensor scanning circuit 300 and outputs the light receiving signals Y1 to Ym to the control unit 50. Here, the circuit configuration of the light receiving unit 30 illustrated in FIG. 10 is not limited to the present aspect, and is common to all aspects.

Figure 11:
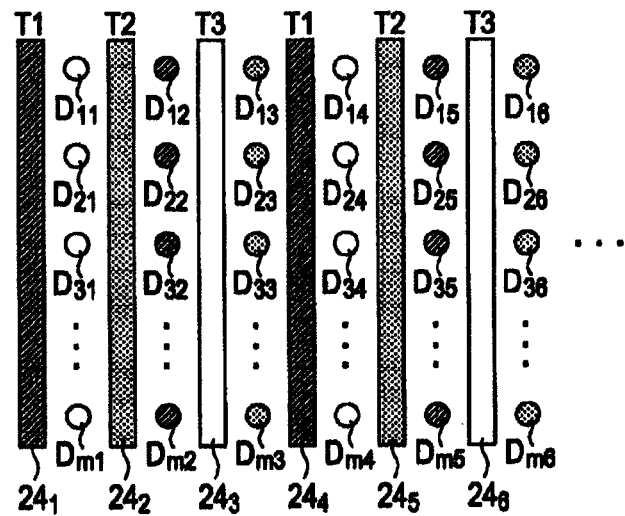
FIG. 11 is a diagram for describing the actions of generating a vein image.

FIG. 11 is a diagram for describing the actions of generating a vein image.

The n cathodes $24_1$ to $24_n$ are divided into a plurality of groups. In the case of the example illustrated in the drawing, the n cathodes $24_1$ to $24_n$ are divided into three groups, wherein the cathodes $24_1$, $24_4$, $24_7$ ... are included in the first group, the cathodes $24_2$, $24_5$, $24_8$ ... are included in the second group, and the cathodes $24_3$, $24_6$, and $24_9$ are included in the third group. Further, the cathode driving circuit 200 successively selects n cathodes $24_1$ to $24_n$ by groups. That is, in the case of the example illustrated in the drawing, the cathode driving circuit 200 selects the cathodes $24_1$, $24_4$, $24_7$ ... that belong to the first group during a time period T1, selects the cathodes $24_2$, $24_5$, $24_8$ ... that belong to the second group during a time period T2, and selects the cathodes $24_3$, $24_6$, $24_9$ ... that belong to the third group during a time period T3.

In such a case, portions that correspond to the cathodes $24_1$, $24_4$, $24_7$ ... out of the organic EL layer 26 emit light in a stripe shape during the time period T1, portions that correspond to the cathodes $24_2$, $24_5$, $24_8$ ... out of the organic EL layer 26 emit light in a stripe shape during the time period T2, and portions that correspond to the cathodes $24_3$, $24_6$, $24_9$ ... out of the organic EL layer 26 emit light in a stripe shape during the time period T3.

On the other hand, the light receiving sensor scanning circuit 300 and the light receiving signal reading circuit 400 read the light receiving signals from all of the light receiving signals D (m×n) every time that the cathode driving circuit 200 successively selects the n cathodes $24_1$ to $24_n$ by groups. Therefore, the light receiving signals for one frame during the time period T1, the light receiving signals for one frame during the time period T2, and the light receiving signals for one frame during the time period T3 are input to the control unit 50.

Incidentally, for example, while a portion that corresponds to the cathode $24_4$ out of the organic EL layer 26 emits light in a stripe shape in a case when the cathode driving signal 200 selects the cathode $24_4$, since each of the two rows of light receiving elements $D_{13}$ to $D_{m3}$ and $D_{14}$ to $D_{m4}$ that are positioned on both sides of the cathode $24_4$ with the cathode $24_4$ therebetween are close to the light emitting regions at this time, the surface reflected light that reflects off the skin of the finger F is included in the reflected light RL that is incident on the light receiving faces.

Therefore, the control unit 50 removes the light receiving signals that are read from the light receiving elements D that are positioned in the vicinity of each light receiving region during the time period T1 from the light receiving signals for one frame in the time period T1, and makes the remainder the light receiving signals for generating a vein image. That is, the control unit 50 removes the light receiving signals that are read from each of the light receiving elements D of the first column, the third column, the fourth column, the sixth column, the seventh column . . . that are positioned on both ends of each of the cathodes 24 (each light emitting region) on the first column, the fourth column, the seventh column . . . that the cathode driving circuit 200 has selected during the time period T1 from the light receiving signals for one frame during the time period T1, and makes the light receiving signals that are read from each of the remaining light receiving elements D of the second column, the fifth column, the eighth column . . . the light receiving signals for generating a vein image.

Further, the control unit 50 removes the light receiving signals that are read from the light receiving elements D that are positioned in the vicinity of each light emitting region during the time period T2 from the light receiving signals for one frame during the time period T2, and makes the remainder the receiving signals for generating a vein image. That is, the control unit 50 removes the light receiving signals that are read from each of the light receiving elements D of the first column, the second column, the fourth column, the fifth column, the seventh column, the eighth column . . . that are positioned on both ends of each of the cathodes 24 (each light emitting region) on the second column, the fifth column, the eighth column . . . that the cathode driving circuit 200 has selected during the time period T2 from the light receiving signals for one frame during the time period T2, and makes the light receiving signals that are read from each of the remaining light receiving elements D of the third column, the sixth column, the ninth column . . . the light receiving signals for generating a vein image.

Similarly, the control unit 50 removes the light receiving signals that are read from the light receiving elements D that are positioned in the vicinity of each light emitting region during the time period T3 from the light receiving signals for one frame during the time period T3, and makes the remainder the receiving signals for generating a vein image. That is, the control unit 50 removes the light receiving signals that are read from each of the light receiving elements D of the second column, the third column, the fifth column, the sixth column, the eighth column, the ninth column . . . that are positioned on both ends of each of the cathodes 24 (each light emitting region) on the third column, the sixth column, the ninth column . . . that the cathode driving circuit 200 has selected during the time period T3 from the light receiving signals for one frame during the time period T3, and makes the light receiving signals that are read from each of the remaining light receiving elements D of the first column, the fourth column, the seventh column . . . the light receiving signals for generating a vein image.

The control unit 50 then generates a vein image by synthesizing the light receiving signals for generating a vein image from the time period T1 (the light receiving signals that are read from each of the light receiving elements D of the second column, the fifth column, the eighth column . . . ), the light receiving signals for generating a vein image from the time period T2 (the light receiving signals that are read from each of the light receiving elements D of the third column, the sixth column, the ninth column . . . ), and the light receiving signals for generating a vein image from the time period T3 (the light receiving signals that are read from each of the light receiving elements D of the first column, the fourth column, the seventh column . . . ). Since it is possible to generate a vein image without using the light receiving signals from the light receiving elements D on which the surface reflected light is incident by synthesizing the light receiving signals for generating a vein image of the time periods T1, T2, and T3 in such a manner, it is possible to prevent a decrease in the capturing precision due to the surface reflected light and to increase the capturing precision of the vein image.

Here, n cathodes $24_1$ to $24_n$ may be divided into three or more groups. For example, a configuration in which the n cathodes $24_1$ to $24_n$ are divided into four groups, the first group includes the cathodes $24_1$, $24_5$, $24_9$ . . . , the second group includes the cathodes $24_2$, $24_6$, $24_{10}$ . . . , the third group includes the cathodes $24_3$, $24_7$, $24_{11}$ . . . , and the fourth group includes the cathodes $24_4$, $24_8$, $24_{12}$ . . . is also possible. In such a case, the control unit 50 removes the light receiving signals that are read from each of the light receiving elements D of the first column, the fourth column, the fifth column, the eighth column, the ninth column . . . that are positioned on both ends of each of the cathodes 24 (each light emitting region) that the cathode driving circuit 200 has selected from the light receiving signals for one frame that is read when the cathode driving circuit 200 has selected each of the cathodes 24 of the first column, the fifth column, the ninth column . . . belonging to the first group, for example, and makes the light receiving signals that are read from each of the remaining light receiving elements D of the second column, the third column, the sixth column, the seventh column . . . the light receiving signals for generating a vein image.

Further, the n cathodes $24_1$ to $24_n$ may be divided into n groups. In such a case, for example, the control unit 50 removes the light receiving signals that are read from each of the light receiving elements D of the first column which are positioned next to the cathode $24_1$ (light emitting region) as well as the light receiving signals that are read from each of the light receiving elements D of the third column and thereafter from the light receiving signals for one frame which are read when the cathode driving signal 200 has selected the cathode $24_1$ of the first column, and makes the light receiving signals that are read from each of the remaining light receiving elements D of the second column the light receiving signals for generating a vein image.

Here, the reason for removing the light receiving signals that are read from each of the light receiving elements D of the first column is to prevent a decrease in the capturing precision due to the surface reflected light. On the other hand, the reason for removing the light receiving signals that are read from each of the light receiving elements D of the third column and thereafter is that since each of the light receiving elements D of the n−1 column or the n column, for example, are far from the light emitting regions, such light receiving elements D are unable to receive the reflected light RL or even if the reflected light RL can be received, the reflected light RL is not of a level that is suited to the generation of a vein image. In such a manner, the control unit 50 may not only remove the light receiving signals that are read from each of the light receiving elements D that are positioned at both ends of one or more cathodes 24 (light emitting regions) that the cathode driving circuit 200 has selected but also remove the light receiving signals that are read from each of the light receiving elements D that are far from the light emitting regions and for which the reflected light RL of a level that is suited to the generation of a vein image cannot be obtained when obtaining the light receiving signals for generating a vein image from the light receiving signals for one frame.

Figure 12:
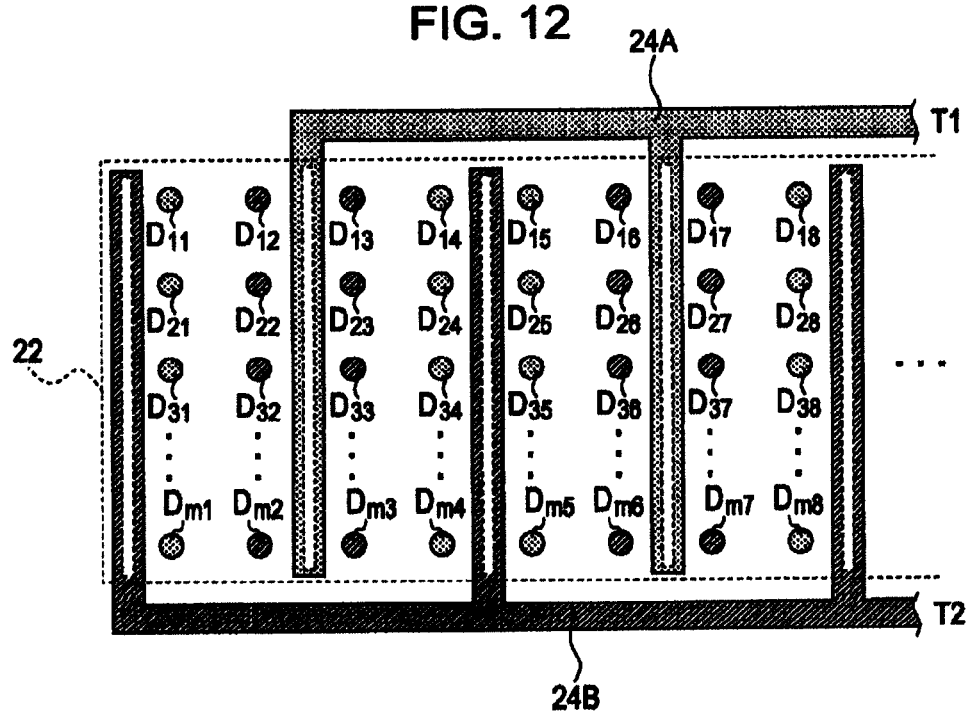
FIG. 12 is a diagram for describing a modification example of the fourth aspect.

Further, as illustrated in FIG. 12, as well as providing two cathodes 24A and 24B with a comb-like shape, by arranging two columns of the light receiving elements D on each separating region between the cathode 24A and the cathode 24B, it is possible to generate one vein image from the light receiving signals for two frames. Here, in the case of the example shown in the drawing, the cathode driving circuit 200 selects the cathode 24A during the time period T1 and selects the cathode 24B during the time period T2. Further, a portion that overlaps the cathode 24A (region indicated by the dotted line in the drawing) out of the organic EL layer 26 during the time period T1 and a portion that overlaps the cathode 24B (region indicated by the dotted line in the drawing) out of the organic EL layer 26 during the time period T2 emit light.

In such a case, the control unit 50 removes the light receiving signals that are read from each of the light receiving elements D of the second column, the third column, the sixth column, the seventh column . . . that are positioned at both ends of the cathode 24A from the light receiving signals for one frame during the time period T1, and makes the light receiving signals that are read from each of the remaining light receiving elements D of the first column, the fourth column, the fifth column, the eighth column . . . the light receiving signals for generating a vein image. Further, the control unit 50 removes the light receiving signals that are read from each of the light receiving elements D of the first column, the fourth column, the fifth column, the eighth column . . . that are positioned at both ends of the cathode 24B from the light receiving signals for one frame during the time period T2, and makes the light receiving signals that are read from each of the remaining light receiving elements D of the second column, the third column, the sixth column, the seventh column . . . the light receiving signals for generating a vein image.

Further, the control unit 50 generates a vein image by synthesizing the light receiving signals for generating a vein image during the time period T1 (the light receiving signals that are read from each of the light receiving elements D of the first column, the fourth column, the fifth column, the eighth column . . . ) and the light receiving signals for generating a vein image during the time period T2 (the light receiving signals that are read from each of the light receiving elements D of the second column, the third column, the sixth column, the seventh column . . . ). In such a case, since a vein image can be generating without using the light receiving elements D on which the surface reflected light is incident by synthesizing the light receiving signals for generating a vein image during the time periods T1 and T2, it is possible to prevent a decrease in the capturing precision due to the surface reflected light and to increase the capturing precision of the vein image. Further, since one vein image can be generated from the light receiving signals for two frames, compared to the case of FIG. 11, it is possible to shorten the amount of time spent in generating a vein image and to reduce the amount of power that is consumed in generating a vein image.

Further, only the light receiving signals for generating a vein image may be read when reading the light receiving signals using the light receiving sensor scanning circuit 300 and the light receiving signal reading circuit 400. For example, in the case of the example illustrated in FIG. 11, the light receiving sensor scanning circuit 300 and the light receiving signal reading circuit 400 exclude each of the light receiving elements D of the first column, the third column, the fourth column, the sixth column, the seventh column . . . that are positioned at both ends of each of the cathodes 24 (each of the light emitting regions) of the first column, the fourth column, the seventh column . . . that the cathode driving circuit 200 has selected during the time period T1 as reading targets, and reads the light receiving signals from each of the remaining light receiving elements D of the second column, the fifth column, the eighth column . . . .

Further, the light receiving sensor scanning circuit 300 and the light receiving signal reading circuit 400 exclude each of the light receiving elements D of the first column, the second column, the fourth column, the fifth column, the seventh column, the eighth column . . . that are positioned at both ends of each of the cathodes 24 (each of the light emitting regions) of the second column, the fifth column, the eighth column . . . that the cathode driving circuit 200 has selected during the time period T2, and reads the light receiving signals from each of the remaining light receiving elements D of the third column, the sixth column, the ninth column . . . . Similarly, the light receiving sensor scanning circuit 300 and the light receiving signal reading circuit 400 exclude each of the light receiving elements D of the second column, the third column, the fifth column, the sixth column, the eighth column, the ninth column . . . that are positioned at both ends of each of the cathodes 24 (each of the light emitting regions) of the third column, the sixth column, the ninth column . . . that the cathode driving circuit 200 has selected during the time period T3, and reads the light receiving signals from each of the remaining light receiving elements D of the first column, the fourth column, the seventh column . . . .

Further, the control unit 50 generates a vein image by synthesizing the light receiving signals that are read during the time period T1, the light receiving signals that are read during the time period T2, and the light receiving signals that are during the time period T3. Since it is also possible to generate a vein image without using the light receiving signals from the light receiving elements D on which the surface reflected light is incident in such a case, it is possible to prevent a decrease in the capturing precision due to the surface reflected light and to increase the capturing precision of the vein image. Further, since it is possible to decrease the number of scans by the light receiving sensor scanning circuit 300 and to decrease the number of readings of the light receiving signals by the light receiving signal reading circuit 400, it is also possible to decrease power consumption.

E. FIFTH ASPECT

According to the fourth aspect described above, not only the cathodes $24_1$ to $24_n$, but also the anodes 22 may be a plurality of anodes that are arranged to be apart from one another, and the anodes to which electric current is supplied may also be able to be selected.

Figure 13:
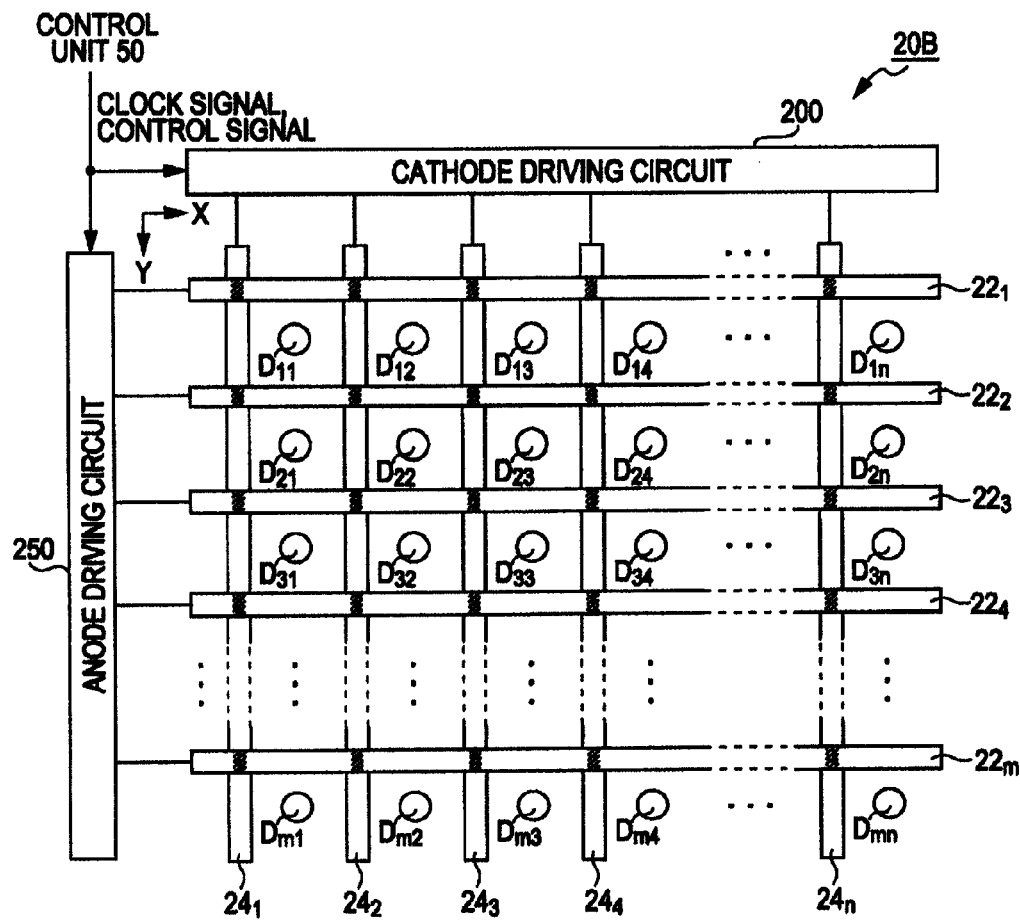
FIG. 13 is a diagram that illustrates a circuit configuration of a light emitting unit of a biometric authentication device according to a fifth aspect.

FIG. 13 is a diagram that illustrates a circuit configuration of a light emitting unit 20B of a biometric authentication device according to a fifth aspect. As illustrated in the drawing, m anodes $22_1$ to $22_m$ that extend in the X axis direction and n cathodes $24_1$ to $24_n$ that extend in the Y axis direction are provided on the light emitting unit 20B. Here, in a case when there is no particular need to distinguish between each of the anodes in the description below, the anodes will be referred to as the anodes 22. Further, according to the present aspect, the arrangement of the plurality of anodes 22, the plurality of cathodes 24, the organic EL layer 26, the plurality of insulating layers 28, and the plurality of light blocking layers BM are the same as the third aspect described above.

Further, other than the cathode driving circuit 200 described in the fourth aspect, an anode driving circuit 250 is provided on the light emitting unit 20B. The anode driving circuit 250 successively selects one or a plurality of anodes 22 to which an electric current is to be supplied from the m anodes $22_1$ to $22_m$ according to a clock signal and a control signal that are supplied from the control unit 50. That is, the organic EL layer 26 emits light by an electric current being supplied between the one or more anodes 22 that are selected by the anode driving circuit 250 and the one or more cathodes 24 that are selected by the cathode driving circuit 200. For example, in a case when the anode driving circuit 250 has selected all of the anodes $22_1$ to $22_m$ and the cathode driving circuit 200 has all selected all of the cathodes $24_1$ to $24_n$, the light emitting regions of the organic EL layer 26 become the portions indicated by the hatching in the drawing. Here, the circuit configuration of the light emitting unit 30 according to the present aspect may be the same as the fourth aspect (FIG. 10).

Figure 14:
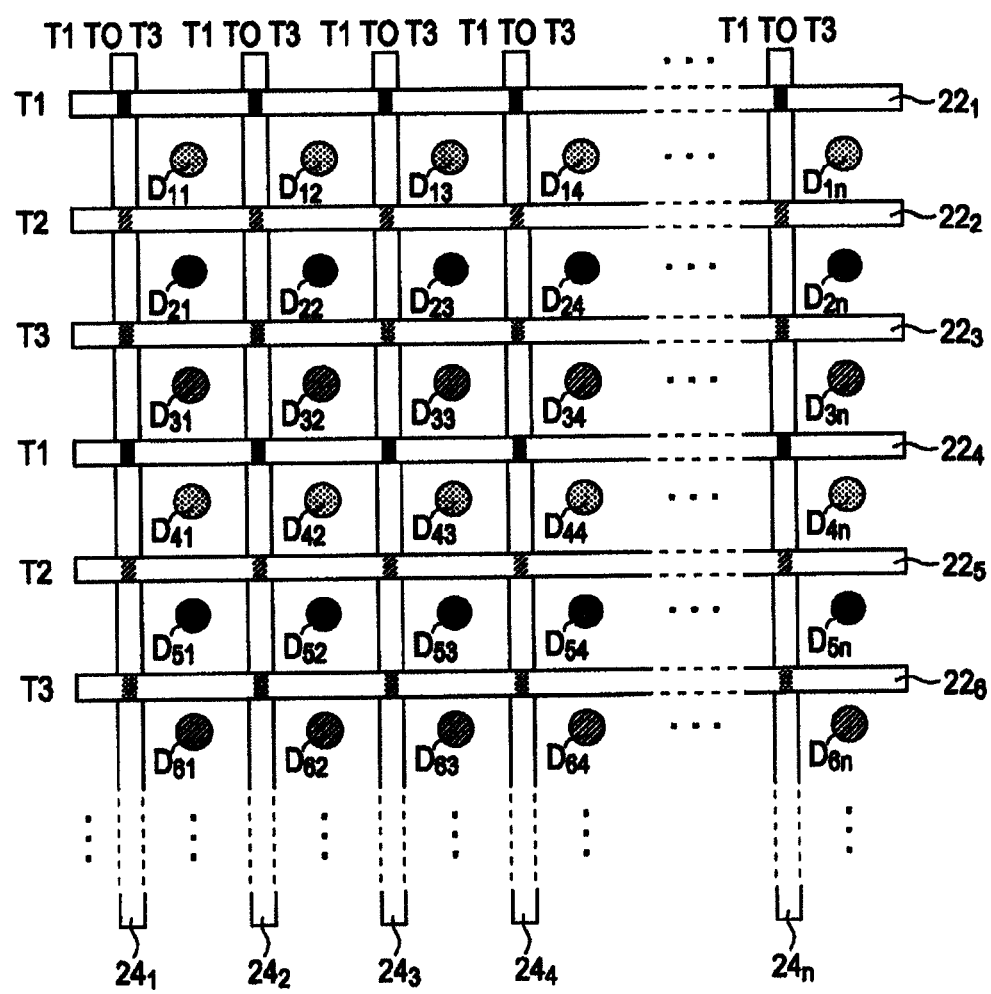
FIG. 14 is a diagram for describing the actions of generating a vein image.

FIG. 14 is a diagram for describing the actions of generating a vein image.

The m anodes $22_1$ to $22_m$ and the n cathodes $24_1$ to $24_n$ are divided into a plurality of groups. In the case of the example illustrated in the drawing, the m anodes $22_1$ to $22_m$ and the n cathodes $24_1$ to $24_n$ are divided into three groups, wherein all of the cathodes $24_1$ to $24_n$ and the anodes $22_1$, $22_4$, $22_7$ ... are included in the first group. Further, all of the cathodes $24_1$ to $24_n$ and the anodes $22_2$, $22_5$, $22_8$ ... are included in the second group. Further, all of the cathodes $24_1$ to $24_n$ and the anodes $22_3$, $22_6$, $22_9$ ... are included in the third group.

The cathode driving circuit 200 successively selects the n cathodes $24_1$ to $24_n$ by groups. Here, in the case of the example illustrated in the drawing, since all of the cathodes $24_1$ to $24_n$ belong to all groups, the cathode driving circuit 200 selects all of the cathodes $24_1$ to $24_n$ for all groups during all of the time periods T1 to T3. Further, the anode driving circuit 250 successively selects the m anodes $22_1$ to $22_m$ by groups. That is, in the case of the example illustrated in the drawing, the anode driving circuit 250 selects the anodes $22_1$, $22_4$, $22_7$ ... that belong to the first group during the time period T1, selects the anodes $22_2$, $22_5$, $22_8$ ... that belong to the second group during the time period T2, and selects the anodes $22_3$, $22_6$, $22_9$ ... that belong to the third group during the time period T3.

In such a case, parts of the portions in which all of the cathodes $24_1$ to $24_n$ and the anodes $22_1$, $22_4$, and $22_7$ ... overlap (regions indicated by the black in the drawing) out of the organic EL layer 26 during the time period T1 emit light.

Further, parts of the portions in which all of the cathodes $24_1$ to $24_n$ and the anodes $22_2$, $22_5$, and $22_8$ ... overlap (regions indicated by the hatching in the drawing) out of the organic EL layer 26 during the time period T2 emit light. Further, parts of the portions in which all of the cathodes $24_1$ to $24_n$ and the anodes $22_3$, $22_6$, and $22_9$ ... overlap (regions indicated by the dots in the drawing) out of the organic EL layer 26 during the time period T3 emit light.

On the other hand, the light receiving sensor scanning circuit 300 and the light receiving signal reading circuit 400 reads the light receiving signals from all of the light receiving elements D (m×n) every time that the cathode driving circuit 200 and the anode driving circuit 250 perform selections in groups. The light receiving signals for one frame during the time period T1, the light receiving signals for one frame during the time period T2, and the light receiving signals for one frame during the time period T3 are therefore input to the control unit 50.

The control unit 50 removes the light receiving signals that are read from the light receiving elements D that are positioned in the vicinity of each of the light emitting regions during the time period T1 from the light receiving signals for one frame during the time period T1, and makes the remainder the light receiving signals for generating a vein image. That is, the control unit 50 removes the light receiving signals that are read from each of the light receiving elements D of the first column, the third column, the fourth column, the sixth column, the seventh column ... that are positioned at both ends (up and down in the drawing) of each of the anodes 22 of the first column, the fourth column, the seventh column ... that the anode driving circuit 250 has selected during the time period T1 from the light receiving signals for one frame during the time period T1, and makes the light receiving signals that are read from each of the remaining light receiving elements D of the second column, the fifth column, the eighth column ... the light receiving signals for generating a vein image.

Further, the control unit 50 removes the light receiving signals that are read from the light receiving elements D that are positioned in the vicinity of each of the light emitting regions during the time period T2 from the light receiving signals for one frame during the time period T2, and makes the remainder the light receiving signals for generating a vein image. That is, the control unit 50 removes the light receiving signals that are read from each of the light receiving elements D of the first column, the second column, the fourth column, the fifth column, the seventh column, the eighth column ... that are positioned at both ends (up and down in the drawing) of each of the anodes 22 of the second column, the fifth column, the eighth column that the anode driving circuit 250 has selected during the time period T2 from the light receiving signals for one frame during the time period T2, and makes the light receiving signals that are read from each of the remaining light receiving elements D of the third column, the sixth column, the ninth column ... the light receiving signals for generating a vein image.

Similarly, the control unit 50 removes the light receiving signals that are read from the light receiving elements D that are positioned in the vicinity of each of the light emitting regions during the time period T3 from the light receiving signals for one frame during the time period T3, and makes the remainder the light receiving signals for generating a vein image. That is, the control unit 50 removes the light receiving signals that are read from each of the light receiving elements D of the second column, the third column, the fifth column, the sixth column, the eighth column, the ninth column ... that are positioned at both ends (up and down in the drawing) of each of the anodes 22 of the third column, the sixth column, the ninth column ... that the anode driving circuit 250 has selected during the time period T3 from the light receiving signals for one frame during the time period T3, and makes the light receiving signals that are read from each of the remaining light receiving elements D of the first column, the fourth column, the seventh column ... the light receiving signals for generating a vein image.

The control unit 50 then generates a vein image by synthesizing the light receiving signals for generating a vein image from the time period T1 (the light receiving signals that are read from each of the light receiving elements D of the second column, the fifth column, the eighth column ... ), the light receiving signals for generating a vein image from the time period T2 (the light receiving signals that are read from each of the light receiving elements D of the third column, the sixth column, the ninth column ... ), and the light receiving signals for generating a vein image from the time period T3 (the light receiving signals that are read from each of the light receiving elements D of the first column, the fourth column, the seventh column ... ). Since it is possible to generate a vein image without using the light receiving signals from the light receiving elements D on which the surface reflected light is incident by synthesizing the light receiving signals for generating a vein image of the time periods T1, T2, and T3 even with the configuration described above, the same effects as the fourth aspect are obtained.

Here, similarly to the case of the fourth aspect, according to the present aspect, the m anodes $22_1$ to $22_m$ and the n cathodes $24_1$ to $24_n$ may be divided into three or more groups. Further, the control unit 50 may remove not only the light receiving signals that are read from each of the light receiving elements D that are positioned in the vicinity of portions in which the one or more anodes 22 that the anode driving circuit 250 has selected and the one or more cathodes 24 that the cathode driving circuit 200 has selected overlap (light emitting regions) but also the light receiving signals that are read from each of the light receiving elements D that cannot obtain a level of the reflected light RL which is suited to the generation of a vein image when obtaining the light receiving signals for generating a vein image from the light receiving signals for one frame.

Further, when reading the light receiving signals using the light receiving sensor scanning circuit 300 and the light receiving signal reading circuit 400, only the light receiving signals for generating a vein image may be read. For example, in the case of the example illustrated in FIG. 14, the light receiving sensor scanning circuit 300 and the light receiving signal reading circuit 400 exclude each of the light receiving elements D of the first column, the third column, the fourth column, the sixth column, the seventh column . . . that are positioned at both ends of each of the anodes 22 (up and down in the drawing) of the first column, the fourth column, the seventh column . . . that the anode driving circuit 250 has selected during the time period T1 as reading targets, and reads the light receiving signals from each of the remaining light receiving elements D of the second column, the fifth column, the eighth column . . . .

Further, the light receiving sensor scanning circuit 300 and the light receiving signal reading circuit 400 exclude each of the light receiving elements D of the first column, the second column, the fourth column, the fifth column, the seventh column, the eighth column . . . that are positioned at both ends of each of the anodes 22 (up and down in the drawing) of the second column, the fifth column, the eighth column . . . that the anode driving circuit 250 has selected during the time period T2 as reading targets, and reads the light receiving signals from each of the remaining light receiving elements D of the third column, the sixth column, the ninth column . . . . Similarly, the light receiving sensor scanning circuit 300 and the light receiving signal reading circuit 400 exclude each of the light receiving elements D of the second column, the third column, the fifth column, the sixth column, the eighth column, the ninth column . . . that are positioned at both ends of each of the anodes 22 (up and down in the drawing) of the third column, the sixth column, the ninth column . . . that the anode driving circuit 250 has selected during the time period T3 as reading targets, and reads the light receiving signals from each of the remaining light receiving elements D of the first column, the fourth column, the seventh column . . . .

Further, the control unit 50 generates a vein image by synthesizing the light receiving signals that are read during the time period T1, the light receiving signals that are read during the time period T2, and the light receiving signals that are during the time period T3. Since it is also possible to generate a vein image without using the light receiving signals from the light receiving elements D on which the surface reflected light is incident in such a case, it is possible to prevent a decrease in the capturing precision due to the surface reflected light and to increase the capturing precision of the vein image. Further, since it is possible to decrease the number of scans by the light receiving sensor scanning circuit 300 and to decrease the number of readings of the light receiving signals by the light receiving signal reading circuit 400, it is also possible to decrease power consumption.

F. SIXTH ASPECT

While a case when the invention is applied to a biometric authentication device has been described in each of the aspects described above, the invention can also be applied to an image scanner that reads an image such a manuscript. In such a case, visible light is used instead of near-infrared light as the irradiation light IL or the reflected light RL. That is, the light emitting unit 20 (organic EL layer 26) emits visible light instead of near-infrared light as the reflected light RL, and the light receiving unit 30 (each light receiving element D) receives visible light instead of near-infrared light as the reflected light RL. Further, the cover glass 10, the lens array LA, the opposing substrate GS, the anode 22, the insulating layer 28, the organic EL layer 26, and the sealing layer 29 are formed by materials with high transmittance with respect to visible light, and the cathode 24 and the light blocking layer BM are formed by materials with a high light blocking property with respect to visible light.

Figure 15A:
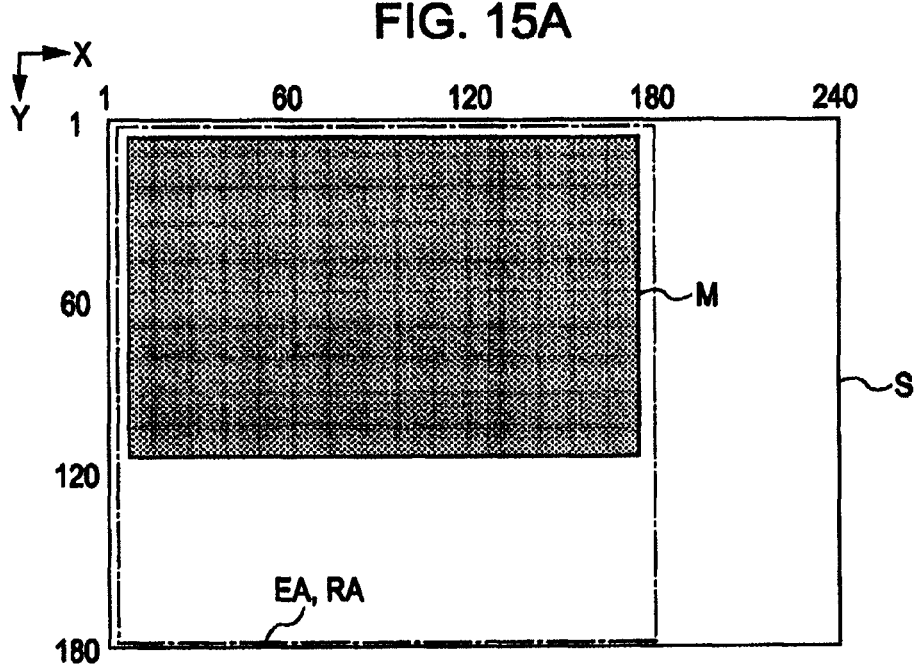
FIGS. 15A and 15B are diagrams that illustrate the light emitting range of irradiation light and the reading range of a light receiving signal according to a sixth aspect.

Incidentally, in a case when the image scanner to which the invention is applied includes the light emitting unit 20A illustrated in FIG. 9 and the light receiving unit 30 included in FIG. 10, it is possible to decrease power consumption by determining a light emitting region of the irradiation light IL and the reading range of the light receiving signals according to the size or position of the manuscript that is placed on the capturing region S. For example, a case when a manuscript M is placed on the capturing region S as illustrated in FIG. 15A is considered. Here, one anode 22 that covers the entire face of the capturing region S and 240 cathodes $24_1$ to $24_{240}$ that extend in the Y axis direction are provided on the capturing region S. Further, 180 (rows)×240 (columns) of light receiving elements $D_{11}$ to $D_{180, 240}$ are arranged on the capturing region S in a matrix pattern.

In such a case, the image scanner first detects the size and position of the manuscript M that is placed on the capturing region S by performing pre-scanning. Here, a pre-scan is to scan the manuscript M with a rough resolution than the main scan before performing the main scan. For example, in a case when a pre-scan is performed, the cathode driving circuit 200 selects the cathodes $24_{10}$, $24_{20}$, $24_{30}$, . . . $24_{240}$ from the 240 cathodes $24_1$ to $24_{240}$. That is, the cathode driving circuit 200 selects a cathode 24 at a rate of one in ten. In so doing, in a case when a pre-scan is performed, an electric current is supplied between each of the 24 cathodes 24 that the cathode driving circuit 200 selects and the anode 22, and the organic EL layer 26 emits light.

Further, in a case when performing a pre-scan, the light receiving sensor scanning circuit 300 and the light receiving signal reading circuit 400 reads the light receiving signals from each of the light receiving elements D of, for example, the 10th column, the 20th column, the 30th column, . . . the 240th column. Here, in a case when a pre-scan is performed, the light receiving sensor scanning circuit 300 and the light receiving signal reading circuit 400 can also read the light receiving signals in the Y axis direction (row direction) by performing thinning as appropriate such as the 10th row, the 20th row, the 30th row, . . . the 180th row. Further, the control unit 50 detects the region on which the manuscript M has been placed based on each of the light receiving signals that are read by the pre-scan. For example, in the case of FIG. 15A, the region on which the manuscript M has been placed is detected as a range from the first column to the 180th column in the X axis direction and a range from the first row to the 120th row in the Y axis direction. If the region on which the manuscript M has been placed is detected in such a manner, the control unit 50 determines a light emitting range EA of the irradiation light IL and a reading range RA of the light receiving signals of a case when the main scan is performed.

For example, in the case of FIG. 15A, the light emitting range EA of the irradiation light IL and the reading range RA of the light receiving signals can be determined to be the range indicated by the dotted chain line in the drawing. In such a case, the control unit 50 determines the cathodes 24 that the cathode driving circuit 200 selects as the cathodes $24_1$ to $24_{180}$ in a case when the main scan is performed. Further, the control unit 50 determines the light receiving elements D from which the light receiving sensor scanning circuit 300 and the light receiving signal reading circuit 400 read the light receiving signals to a total of 32400 light receiving elements $D_{11}$ to $D_{180, 180}$ from the first column to the 180th column in a case when the main scan is performed.

Therefore, since the cathode driving circuit 200 selects the cathodes $24_1$ to $24_{180}$ in the main scan, the portions that correspond to the cathodes $24_{181}$ to $24_{240}$ do not have to cause the organic EL layer 26 to emit light. Further, since the light receiving sensor scanning circuit 300 and the light receiving signal reading circuit 400 read the light receiving signals from a total of 32400 light receiving elements $D_{11}$ to $D_{180, 180}$ from the first column to the 180th column in the main scan, the light receiving signals from a total of 10800 light receiving elements $D_{1, 181}$ to $D_{180, 240}$ from the 181st column to the 240th column do not have to be read. It is therefore possible to reduce the power consumption of the image scanner.

Here, in the case of FIG. 15A, the control unit 50 can determine the light receiving elements D from which the light receiving sensor scanning circuit 300 and the light receiving signal reading circuit 400 read the light receiving signals when the main scan is performed to be a total of 21600 light receiving elements $D_{11}$ to $D_{120, 180}$ from the first column to the 180th column and from the first row to the 120th row. In such a case, since it is possible to narrow the reading range RA of the light receiving signals, power consumption can be reduced further.

Figure 15B:
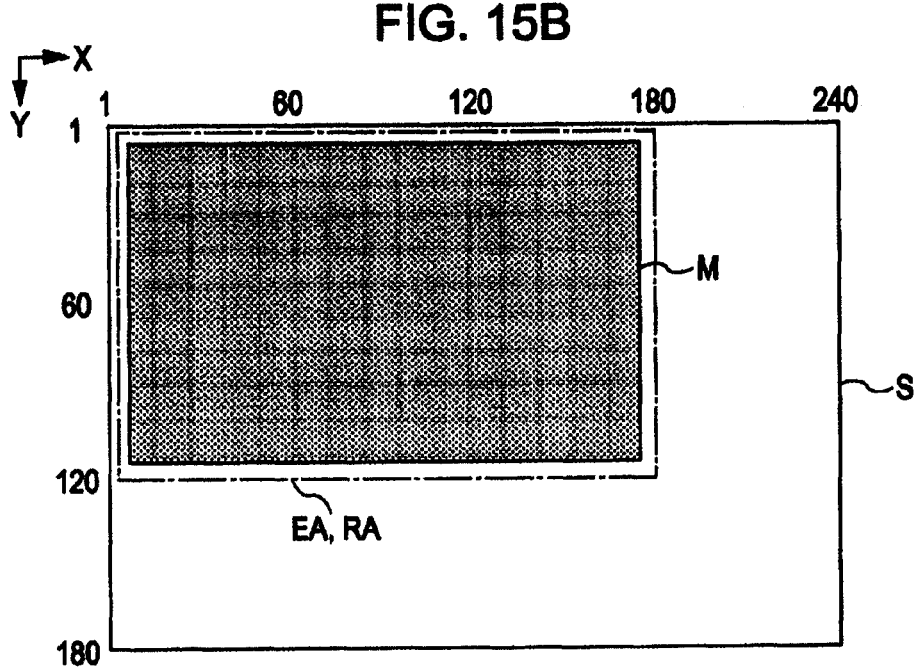

Further, even in a case when the image scanner to which the invention is applied includes the light emitting unit 20B illustrated in FIG. 13 and the light receiving unit 30 illustrated in FIG. 10, power consumption can be reduced by determining the light emitting range EA of the irradiation light IL and the reading range RA of the light receiving signals according to the size and position of the manuscript that is placed on the capturing region S. For example, a case when the manuscript illustrated in FIG. 15B is placed on the capturing region S is considered. Here, 180 anodes $22_1$ to $22_{180}$ that extend in the X axis direction and 240 cathodes $24_1$ to $24_{240}$ that extend in the Y axis direction are provided in the capturing region S. Further, 180 (rows)×240 (columns) light receiving elements $D_{11}$ to $D_{180, 240}$ are arranged in the capturing region S in a matrix pattern.

Even in such a case, the image scanner detects the size and position of the manuscript M that is placed on the scanning region S by performing a pre-scan. For example, in a case when a pre-scan is performed as described above, the cathode driving circuit 200 selects the cathodes $24_{10}$, $24_{20}$, $24_{30}$, ... $24_{240}$. Further, in a case when a pre-scan is performed, the anode driving circuit 250 selects, for example, the anodes $22_{10}$, $22_{20}$, $22_{30}$, ... $22_{180}$ from 180 anodes $22_1$ to $22_{180}$. That is, the anode driving circuit 250 also selects the anodes 22 at a rate of one in ten. In so doing, in a case when a pre-scan is performed, an electric current is supplied between each of the 18 anodes 22 that the anode driving circuit 250 has selected and each of a total of 24 cathodes 24 that the cathode driving circuit 200 has selected, and the organic EL layer 26 emits light.

Further, in a case when a pre-scan is performed, the light receiving sensor scanning circuit 300 and the light receiving signal reading circuit 400 reads the light receiving signals from a total of 432 light receiving elements D that are at positions in which each of the scan lines of the 10th column, the 20th column, the 30th column, ... 240th column and each of the reading lines of the 10th row, the 20th row, the 30th row, ... the 180th row intersect. Further, the control unit 50 detects the region in which the manuscript M is placed based on each of the light receiving signals that are read by the pre-scan, and determines the light emitting range EA of the irradiation light IL and the reading range RA of the light receiving signals in a case when the main scan is performed according to the detected region.

For example, in the case of FIG. 15B, the light emitting range EA of the irradiation light IL and the reading range RA of the light receiving signals can be determined to be the range indicated by the dotted chain line in the drawing. In such a case, the control unit 50 determines the cathodes 24 that the cathode driving circuit 200 selects when the main scan is performed to be the cathodes $24_1$ to $24_{180}$. Further, the control unit 50 determines the anodes 22 that the anode driving circuit 250 selects in a case when the main scan is performed to be the anodes $22_1$ to $22_{120}$. Further, the control unit 50 determines the light receiving elements D that the light receiving sensor scanning circuit 300 and the light receiving signal reading circuit 400 read in a case when the main scan is performed to be a total of 21600 light receiving elements $D_{11}$ to $D_{120, 180}$ from the first column to the 180th column and from the first row to the 120th row.

Therefore, since the cathode driving circuit 200 selects the cathodes $24_1$ to $24_{180}$ and the anode driving circuit 250 selects the anodes $22_1$ to $22_{120}$ in the main scan, the portions that correspond to the cathodes $24_{181}$ to $24_{240}$ and the portions that correspond to the anodes $22_{121}$ to $22_{180}$ do not have to cause the organic EL layer 26 to emit light. Further, since the light receiving sensor scanning circuit 300 and the light receiving signal reading circuit 400 read the light receiving signals from a total of 21600 light receiving elements $D_{11}$ to $D_{120, 180}$ from the first column to the 180th column and from the first row to the 120th row in the main scan, the light receiving signals from each of the light receiving elements D from the 181st column to the 240th column and each of the light receiving elements D from the 121st row to the 180th row (total of 21600) do not have to be read. Therefore, since the light emitting range EA of the irradiation light IL and the reading range RA of the light receiving signals can be narrowed compared to the case of FIG. 15A, power consumption can be reduced further.

Figure 16:
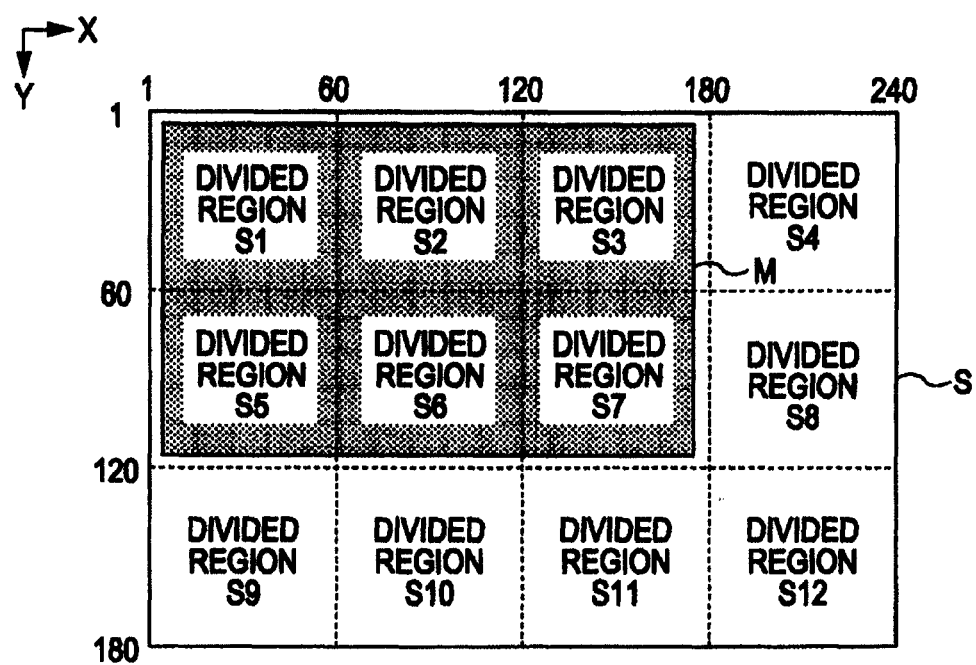
FIG. 16 is a diagram for describing a modification example of the sixth aspect.

Here, in a case when the light emitting range EA of the irradiation light IL and the reading range RA of the light receiving signals are determined by performing a pre-scan, by performing driving (light emitting control and reading control) to remove the influence of the surface reflected light described in the fourth and fifth aspects described above in a case when the main scan is performed, the capturing precision of the vein image can be increased. Further, for example, the capturing region S is divided in advance into 12 divided regions S1 to S12 as illustrated in FIG. 16, and as a result of performing a pre-scan, in a case when the region in which the manuscript M is placed is the divided regions S1 to S3 and S5 to S7, the main scan may be performed by determining the light emitting range EA of the irradiation light IR and the reading range RA of the light receiving signals to be the divided regions S1 to S3, S5 to S7, and S9 to S11 (or the divided regions S1 to S3 and S5 to S7).

Further, even with a biometric authentication device, power consumption can be reduced by detecting the region in which the finger F is placed out of the capturing region S by performing a pre-scan and determining the light emitting range EA of the irradiation light IL and the reading range RA of the light receiving signals in a case when the main scan is performed according to the detected region.

G. MODIFICATION EXAMPLES

The invention is not limited to each of the aspects described above, and for example, the modification examples below are possible. Further, two or more of the modification examples described above may be combined as appropriate.

Modification Example 1

For example, in order to compensate for changes in the photoelectric conversion characteristics of the light receiving elements D due to the light receiving amount (integrated amount) or in order to obtain the values of the light receiving signals in a state in which no reflected light RL is incident as reference values, light receiving elements D of which the upper sides of the light receiving faces are completely covered by the light blocking layers BM may be provided on the end portion of the capturing region. In such a manner, the structure according to the invention does may not necessarily be applied to all light receiving elements D, and it is sufficient if the structure according to the invention is applied to at least one or more of the light receiving elements D. That is, in the case of the first aspect, it is sufficient if there is at least one or more of each of an opening portion of the cathode 24, the light receiving element D, the light blocking layer BM (opening portion), and the insulating layer 28. Further, in the case of the second aspect, it is sufficient if there are at least two or more cathodes 24' and if there is at least one or more of each of the light receiving element D, the light blocking layer BM' (opening portion), and the insulating layer 28'.

Modification Example 2

Figure 17:
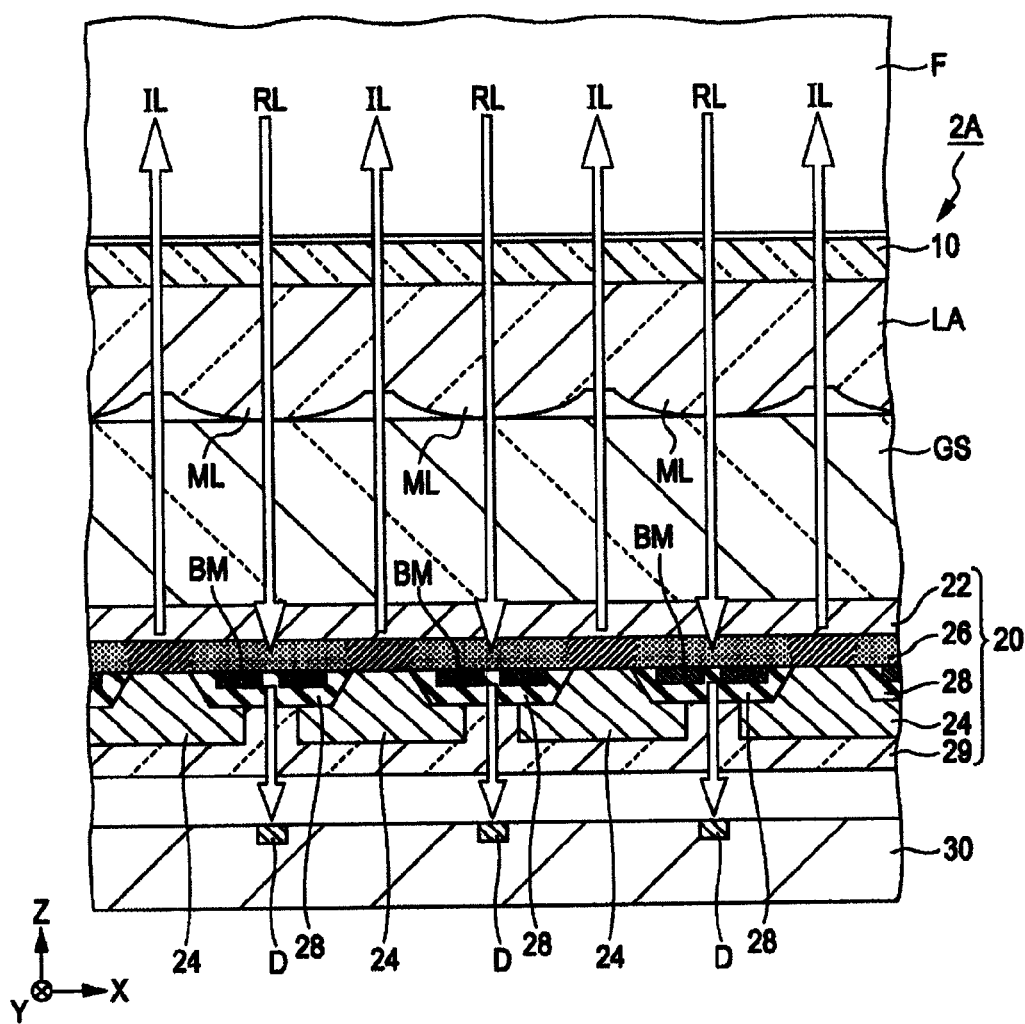
FIG. 17 is a cross-sectional diagram (modification example) of a sensing unit.
Figure 18:
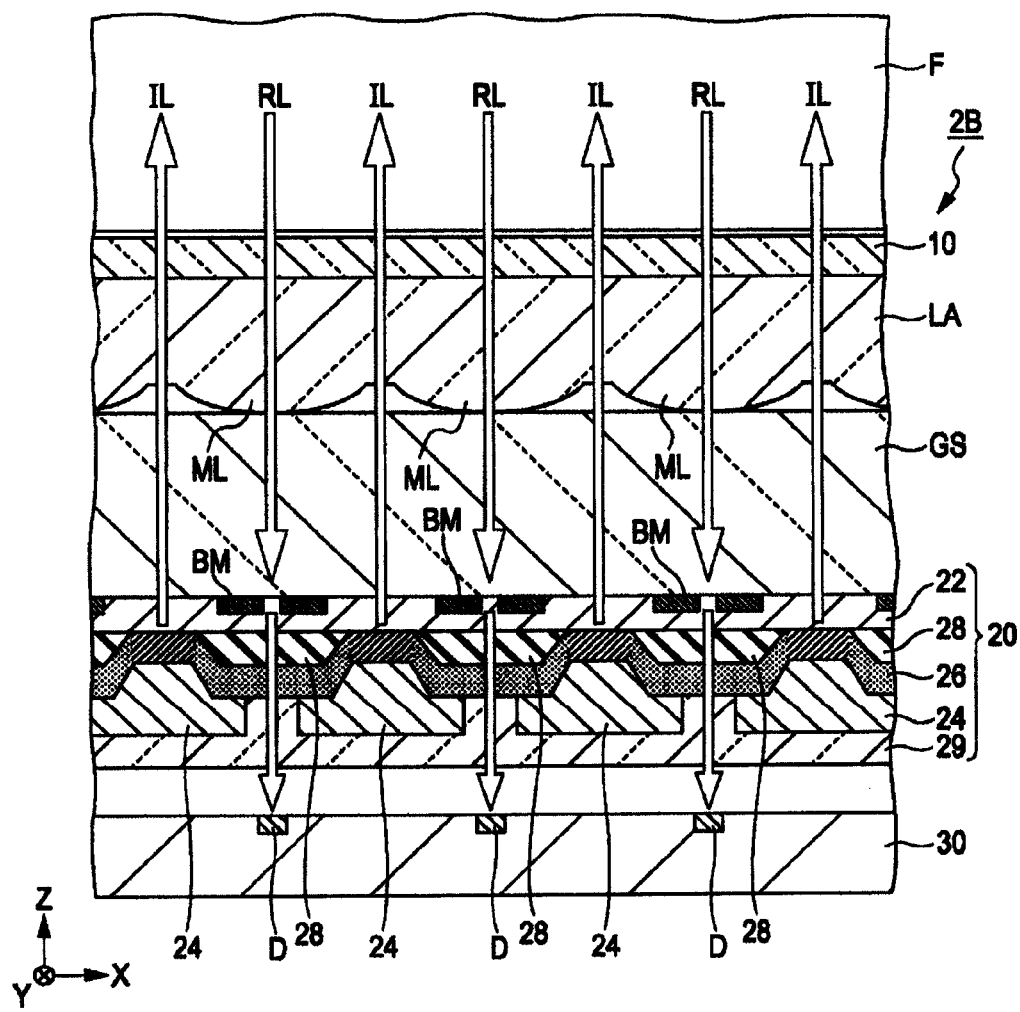
FIG. 18 is another cross-sectional diagram (modification example) of a sensing unit.
Figure 19A:
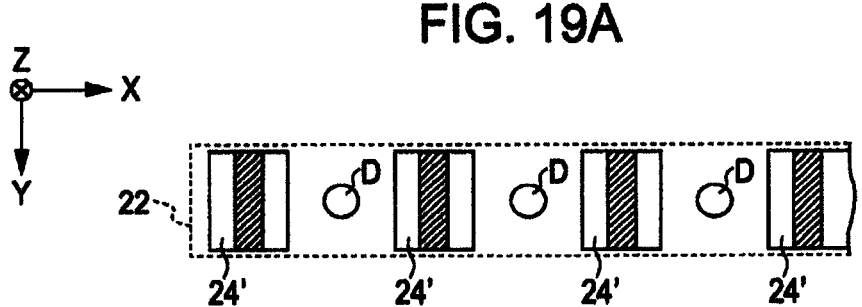
FIGS. 19A and 19B are diagrams that illustrate a modification example of an arrangement of anodes, cathodes, and light receiving elements.
Figure 19B:
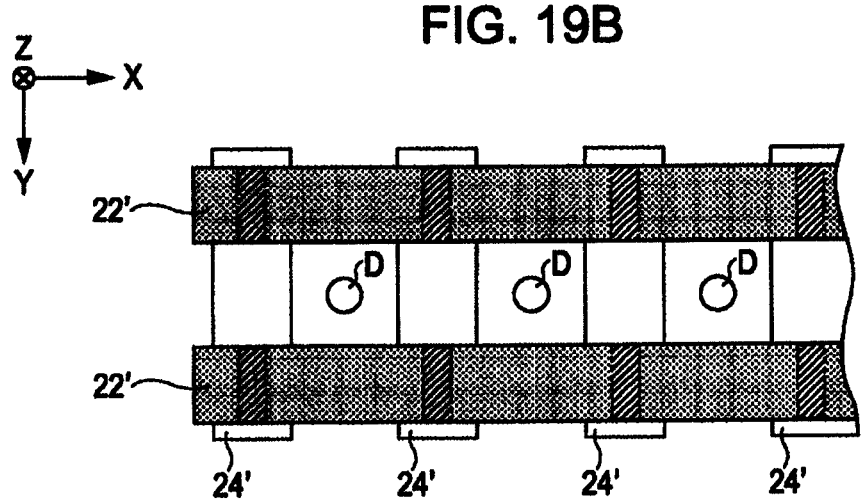

The light blocking layer BM may be formed by a material with a high light blocking property with respect to near-infrared light and a high insulation property. Further, it is desirable that the light blocking layer BM and the cathode 24 be formed of a material with low reflectivity with respect to near-infrared light. Further, as illustrated in FIG. 17, the light blocking layer BM and the insulating layer 28 may be provided on the lower side of the organic EL layer 26. Further, in such a configuration, a second insulating layer may be provided together on the upper side of the organic EL layer 26. Further, as illustrated in FIG. 18, the light blocking layer BM may be provided on the lower face of the opposing substrate GS. Further, the polarity of the anode 22 and the cathode 24 may be reversed. Further, as the light emitting layer, other than the organic EL layer 26, a hole transporting layer, a hole injecting layer, an electron transporting layer, an electron injecting layer, or the like may be included, and the light emitting layer may be an inorganic EL material, a light emitting polymer, or the like instead of an organic EL material. Further, the light emitting layer may be a voltage driven type in which light is emitted by the application of a voltage. Further, the shapes of the light receiving face of the light emitting element D and the opening portion the light blocking layer BM are not limited to circles, and may be an arbitrary shape such as an ellipse, a rectangle, or a hexagon. The shape of the opening portion of the cathode 24, the shape (external shape) of the light blocking BM, or the shape (external shape) of the insulating layer 28 may also be arbitrary shapes without being limited to squares or rectangles. Further, the size of the light receiving face of the light receiving element D and the size of the opening portion of the light blocking layer BM may be larger for the opening portion than the light receiving face, or both may have the same size. Further, while it is desirable that the center (or the center of gravity) of the light receiving face of the light receiving element D be positioned within the opening portion of the light blocking layer BM when viewed in a plan view from the cover glass 10 side, it is sufficient if at least a portion of the light receiving face is positioned within the opening portion. Further, the arrangement pattern of the light receiving elements D or the opening portions is not limited to a matrix pattern. For example, the light receiving elements D and the opening portions may be arranged to create a black and white arrangement pattern of a chess pattern (checkered pattern). Further, the invention may be applied to a sweeping type biometric authentication device. In such a case, for example, as illustrated in FIGS. 19A and 19B, a plurality of light receiving elements D may be lined up in one line along the X axis direction. Further, in such a case, only one opening portion may be provided on each light blocking layer BM. Such modification examples can be applied to each of the aspects described above.

Modification Example 3

The parts of a living body which become targets for vein authentication may be the palm of a hand, the back of a hand, the eyes, or the like. Further, a band-pass filter (optical filter) that blocks light other than near-infrared light may be provided. For example, a band-pass filter can be provided between the opposing substrate GS and the anode 22 or between the cover glass 10 and the lens array 10. Further, visible light may be used instead of near-infrared light and the invention may be applied to a biometric authentication device that performs biometric authentication based on finger prints or irises.

In such a case, the light emitting unit 20 (organic EL layer 26) emits visible light as the irradiation light IL. Further, the light receiving unit 30 (each light receiving element D) receives visible light as the reflected light RL. Further, the cover glass 10, the lens array LA, the opposing substrate GS, the anode 22, the insulating layer 28, the organic EL layer 26, and the sealing layer 29 are formed of materials with high transmittance with respect to visible light, and the cathode 24 and the light blocking layer BM are formed of materials with a high light blocking property with respect to visible light. Such modification examples can be applied to each of the aspects except for the sixth aspect.

Modification Example 4

The invention can be applied, for example, to a personal computer, a mobile phone, or the like with a biometric authentication function. Further, other than an image scanner, the invention can be applied to an image reading device such as a photocopier, a facsimile, or a barcode reader. Here, even in a case when the invention is applied to an image reading device, visible light is used instead of near-infrared light as the irradiation light IL or the reflected light RL.

The entire of Japanese Patent Application No. 2011-084243, filed Apr. 6, 2011 is expressly incorporated by reference herein.

What is claimed is:

1. A sensing device comprising a first electrode, a second electrode in which a first opening portion is formed, a light blocking layer in which a second opening portion is formed, an organic EL layer that includes a light emitting unit and that is formed between the first electrode and the second electrode, and a light receiving unit, in which light from the light emitting unit is irradiated on a subject and reflected light from the subject is received by the light receiving unit, wherein the light emitting unit is a part of the organic EL layer that is wedged between the first electrode and the second electrode, the first electrode and the organic EL layer transmit the irradiated light and the reflected light, the second electrode and the light blocking layer block the irradiated light and the reflected light, the light blocking layer is positioned in the first electrode or between the first electrode and the second electrode, and in plan view from the subject side, the light blocking layer overlaps the first opening portion and the second opening portion is positioned within the first opening portion, and the light receiving unit is positioned further from the subject side than the second electrode, and in plan view from the subject side, the light receiving unit is positioned within the second opening portion.

2. The sensing device according to claim 1, wherein the irradiated light and the reflected light are near-infrared light.

3. The sensing device according to claim 1, further comprising a micro lens, wherein the reflected light that is entered into the receiving unit is through the micro lens.

4. The sensing device according to claim 1, wherein a light receiving face of the light receiving unit is a circuit shape.

5. An electronic apparatus comprising the sensing device according to claim 1.

* * * * *